US012268406B2

(12) United States Patent
Matilla

(10) Patent No.: US 12,268,406 B2
(45) Date of Patent: Apr. 8, 2025

(54) ACTUATION COMBINER MECHANISM AND MOTOR FOR A SURGICAL TOOL

(71) Applicant: Verb Surgical Inc., Santa Clara, CA (US)

(72) Inventor: Jose Luis de Cordoba Matilla, Malaga (ES)

(73) Assignee: Verb Surgical Inc., Santa Clara, CA (US)

( * ) Notice: Subject to any disclaimer, the term of this patent is extended or adjusted under 35 U.S.C. 154(b) by 454 days.

(21) Appl. No.: 17/742,052

(22) Filed: May 11, 2022

(65) Prior Publication Data

US 2023/0363782 A1    Nov. 16, 2023

(51) Int. Cl.
*A61B 17/29* (2006.01)
*A61B 17/00* (2006.01)
(Continued)

(52) U.S. Cl.
CPC .......... *A61B 17/2909* (2013.01); *A61B 34/35* (2016.02); *A61B 34/76* (2016.02);
(Continued)

(58) Field of Classification Search
CPC .......... A61B 2017/00398; A61B 2017/00402; A61B 2017/2909; A61B 2017/2912; A61B 2017/2913; A61B 2017/2915; A61B 2017/2916; A61B 2017/2919; A61B 2017/292; A61B 2017/2922; A61B 2017/2923; A61B 2017/2925; A61B 2017/2929; A61B 2017/2932; A61B 2017/2933; A61B 2017/2934; A61B 2017/2936; A61B 2017/2939; A61B 2017/294; A61B 2017/2941; A61B 2017/2943; A61B 2017/2947; A61B 2017/2845; A61B 34/35; A61B 34/37; A61B 34/76; A61B 17/29; A61B 17/2909;
(Continued)

(56) References Cited

U.S. PATENT DOCUMENTS 7,367,485 B2    5/2008    Shelton, IV et al.
9,370,358 B2 *  6/2016    Shelton, IV ......... A61B 17/068
(Continued)

FOREIGN PATENT DOCUMENTS

CN    213031629 U    4/2021
WO    2020/040295 A1    2/2020

OTHER PUBLICATIONS

International Search Report and Written Opinion received for PCT Patent Application No. PCT/IB2023/054793, mailed on Aug. 28, 2023, 14 pages.
(Continued)

*Primary Examiner* — Kelly J Bekker
*Assistant Examiner* — Alexis D Amechi
(74) *Attorney, Agent, or Firm* — Aikin & Gallant, LLP

(57) ABSTRACT

A surgical tool for a surgical robotic system, the surgical tool comprising: a surgical tool grasper having a jaw operable to perform a surgical procedure; a handle coupled to the surgical tool grasper and having a lever operable to actuate the jaw; and an actuation combiner mechanism coupled to the lever and operable to combine an actuation force output of the lever with an actuation force output of a motor to control the operation of the jaw or the lever.

20 Claims, 14 Drawing Sheets

(51) Int. Cl.
*A61B 34/00* (2016.01)
*A61B 34/35* (2016.01)

(52) U.S. Cl.
CPC ............... *A61B 2017/00398* (2013.01); *A61B 2017/2919* (2013.01)

(58) Field of Classification Search
CPC . A61B 17/2919; A61B 17/28; A61B 17/2841; A61B 17/00; A61B 17/292; A61B 17/2922
See application file for complete search history.

(56) References Cited

U.S. PATENT DOCUMENTS

| | | |
|---|---|---|
| 2009/0312773 A1 | 12/2009 | Cabrera et al. |
| 2011/0040308 A1 | 2/2011 | Cabrera et al. |
| 2012/0116260 A1* | 5/2012 | Johnson .................. A61B 18/14 601/2 |
| 2014/0276736 A1 | 9/2014 | Worrell et al. |
| 2014/0364852 A1* | 12/2014 | Worrell .............. A61B 18/1447 606/51 |
| 2015/0209059 A1* | 7/2015 | Trees ................. A61B 18/1445 606/205 |
| 2015/0351747 A1 | 12/2015 | Martin et al. |
| 2016/0089175 A1* | 3/2016 | Hibner ................ A61B 17/282 606/205 |
| 2019/0000482 A1 | 1/2019 | Hu et al. |
| 2019/0183484 A1 | 6/2019 | Malkowski et al. |
| 2021/0177407 A1* | 6/2021 | Williams ........... A61B 17/0686 |
| 2021/0378661 A1 | 12/2021 | Malkowski et al. |
| 2022/0296263 A1 | 9/2022 | Hirata |
| 2023/0355239 A1* | 11/2023 | Chowaniec ...... A61B 17/07207 |

OTHER PUBLICATIONS

Non-Final Office Action received in U.S. Appl. No. 17/742,009, mailed on Jan. 29, 2025, 21 pages.

Non-Final Office Action for U.S. Appl. No. 17/742,009 mailed Aug. 27, 2024, 17 pages.

* cited by examiner

ACTUATION COMBINER MECHANISM AND MOTOR FOR A SURGICAL TOOL

TECHNICAL FIELD

This disclosure relates generally to the field of robotic surgery and, more particularly, to surgical tools, systems and methods having an actuation combiner mechanism that allows for manual adjustment of sealing forces and enables motorization.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools, for example a surgical stapler and/or an energy device, and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator.

SUMMARY

Aspects of the disclosure include surgical tools having an actuation combiner mechanism that allows for manual adjustment of sealing forces and enables motorization. Representatively, the actuation combiner mechanism combines the actuation and forces of two input links to one output link that controls aspects of the surgical tool. In some aspects, one of the input links is coupled to the closure lever and the other input link is coupled to a combiner/lever adjustment mechanism, preloaded spring or a motor for motorized input or actuation. In some aspects, having an independent input for an adjustment mechanism, preloaded spring or motor allows for improved, enhanced and/or new functionalities on the tool, both for manual or motor actuation while also allowing for haptic feedback on the closure lever. Representative improved, enhanced and/or new functionalities may include, but are not limited to, improved sealing, tissue property identification, motor sealing, improved ergonomics, jaw control, overstuffed jaw detection, assisted lever closure, user adjustable sealing force, jaw gap and force measurements. In some aspects, the combiner mechanism allows changing the applied force on the tissue allowing the same tool to perform different level of forces during sealing. In addition, the introduction of a motor allows force sensing, which can be used for performing better sealing by controlling the applied clamping force. Since the applied force level is defined by the motor, this allows for fine tuning of the applied clamping force, which can reduce sealing issues. For example, motor assisted quick movements may help to prevent tissues sticking to the jaw. In addition, motor assisted movement can also allow better tissue grasping and manipulation. Still further, the motorization of the jaw can be used to perform a modulated load which applies high and low forces over several cycles in order to soften hard/fatty tissues and remove excess fluid. This, in turn, allows for better sealing as well as reducing the probability of the tissue getting stuck to the jaw by performing a cycle before the sealing is completed. Knowing the load profiles allows the tool to clamp to a tissue at a low force and once the sealing procedure is triggered, run that profile which can be a ramp up to a higher force, and once it is completed go back to the initial force. This allows the user to close the jaw with minimal effort required and perform much higher clamping force when sealing. Motorization also allows advance measurements such as the tissue properties like stiffness and perform plots of data, such as jaw gap versus jaw load, and other measurements that could help to identify different types of tissue and monitor sealing cycles.

The surgical tool may be any surgical tool having a surgical tool grasper used to perform surgical procedures or operations. Representatively, in one aspect, the surgical tool may be an energy tool, a harmonic tool, a stapler, or any other surgical tool or device having a handle with a lever latching mechanism to facilitate control and/or manipulation of the surgical tool (e.g., application of energy using an energy tool) or device by the surgeon. An "energy tool" or "energy device" as used herein is intended to refer to any surgical instrument that can be used to manipulate a tissue by applying energy during a surgical procedure. For example, an energy tool or device may be any surgical instrument that can emit an energy sufficient to cut, dissect, burn, seal, coagulate, desiccate, fulgurate and/or achieve homeostasis of the tissue upon contact with the tissue. The energy tool or device may apply energy in the form of high frequencies, radio frequencies, ultrasonic waves, microwaves, or the like. In some aspects, the energy tool may include a surgical tool grasper having a jaw that is inserted into the patient to perform the surgical procedure and is connected to a handle having a lever or trigger that controls the grasper and opening or closing of the jaw. For example, during operation, the surgeon may hold the handle and manipulate the lever or trigger to control a clamping of the grasper or jaw on a tissue, or the application of energy from the grasper of jaw. Representatively, in some aspects, the user may squeeze the lever toward a closed position to cause the grasper or jaw to close or clamp onto the tissue and/or emit energy. Said another way, squeezing of the lever toward the handle (or closed position) may cause the anvils that form the top and bottom of the jaw to become closer together and therefore the size of the jaw gap to be reduced. The opposite operation, for example moving of the lever or trigger away from the handle toward an open position may cause the grasper or jaw to open, or be less closed, or reduce the application of energy. Said another way, releasing the lever, or otherwise moving it away from the handle toward an open position, may cause the anvils that form the top and bottom of the jaw to become farther apart and therefore the size of the jaw gap to be increased. In still further aspects, the lever may latch (or otherwise be secured) in the closed position and/or open position and remain latched until the user applies an opposite force pushing the lever or trigger away from the handle. The lever or trigger may then remain in the latched position until the user applies a force pulling the lever or trigger toward the handle back to the closed position or pushing the lever or trigger away from the handle to the open position. In some aspects, the combiner mechanism may be coupled to the lever or trigger to enhance or modify an operation of the lever, or components controlled by the lever such as the jaw.

An aspect of the disclosure is directed to a surgical tool for a surgical robotic system, the surgical tool comprising: a surgical tool grasper having a jaw operable to perform a surgical procedure; a handle coupled to the surgical tool grasper and having a lever operable to actuate the jaw; and an actuation combiner mechanism coupled to the lever and operable to combine an actuation force output of the lever with an actuation force output of a motor to control the operation of the jaw or the lever. In some aspects, the actuation combiner mechanism comprises a combiner wheel that rotates about a center pivot point and couples a lever input link from the lever and a motor input link from the motor to an output link that controls the operation of the jaw or the lever. In some aspects, the lever input link is coupled to the combiner wheel at a first pivot point that is a first radial distance from the center pivot point and the motor input link is coupled to the combiner wheel at a second pivot point that is a second radial distance from the center pivot point. In some aspects, the combined actuation force output of the output link is selected by modifying a ratio of the first radial distance and the second radial distance. The combiner wheel may include a radially oriented slot and the first pivot point is defined by a pin operable to slide within the radially oriented slot to modify a distance of the first pivot point to the combiner wheel output center pivot point. The motor further comprises a sensor for determining a position of the jaw during operation. In some aspects, the sensor is an encoder that detects a position of the motor to indirectly determine the position of the jaw during operation. In some aspects, the motor further comprises an actuator operable to output a micro modulation frequency to an output link of the actuation combiner mechanism. The system may further include a haptic feedback mechanism that provides a haptic output to a user corresponding to the operation of the jaw or the lever.

In other aspects, a motorized surgical tool for a surgical robotic system includes a surgical tool grasper having a jaw operable to perform a surgical procedure; a handle coupled to the surgical tool grasper and having a lever operable to actuate the jaw; and an actuation combiner mechanism comprising a combiner wheel, a lever input link coupled to the combiner wheel at a first pivot point and coupled to the lever, a motor input link coupled to the combiner wheel at a second pivot point and coupled to a motor, and an output link coupled to a yoke that causes the jaw to open or close. In some aspects, a movement of the lever to a closed position produces an actuation force output of the lever in a first direction that causes the yoke to move the jaw to a closed position. In some aspects, a movement of the lever to an open position produces an actuation force output of the lever in a second direction that causes the yoke to move the jaw to an open position. In some aspects, the combiner mechanism combines the actuation force output of the lever in the first direction or the second direction with an actuation force output of the motor to move the jaw. In some aspects, the combined actuation force output of the lever and the motor is operable to be modified by modifying a ratio of a first radial distance of the first pivot point to a center of the combiner wheel and a second radial distance of the second pivot to the center of the combiner wheel. The combiner wheel may further include a radially oriented slot and a pin defining the first pivot point is adjustable within the slot to modify the first radial distance. In some aspects, the radially oriented slot is curved. In some aspects, the combiner wheel comprises an elongated shape. The motor further comprises an encoder that detects a position of the motor to indirectly determine the position of the jaw during operation. In other aspects, the motor further comprises an actuator operable to output a micro modulation frequency to the output link. In some aspects, a haptic feedback mechanism provides a haptic output to a user corresponding to the operation of the jaw.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect in this disclosure are not necessarily to the same aspect, and they mean at least one.

DETAILED DESCRIPTION

Figure 1:
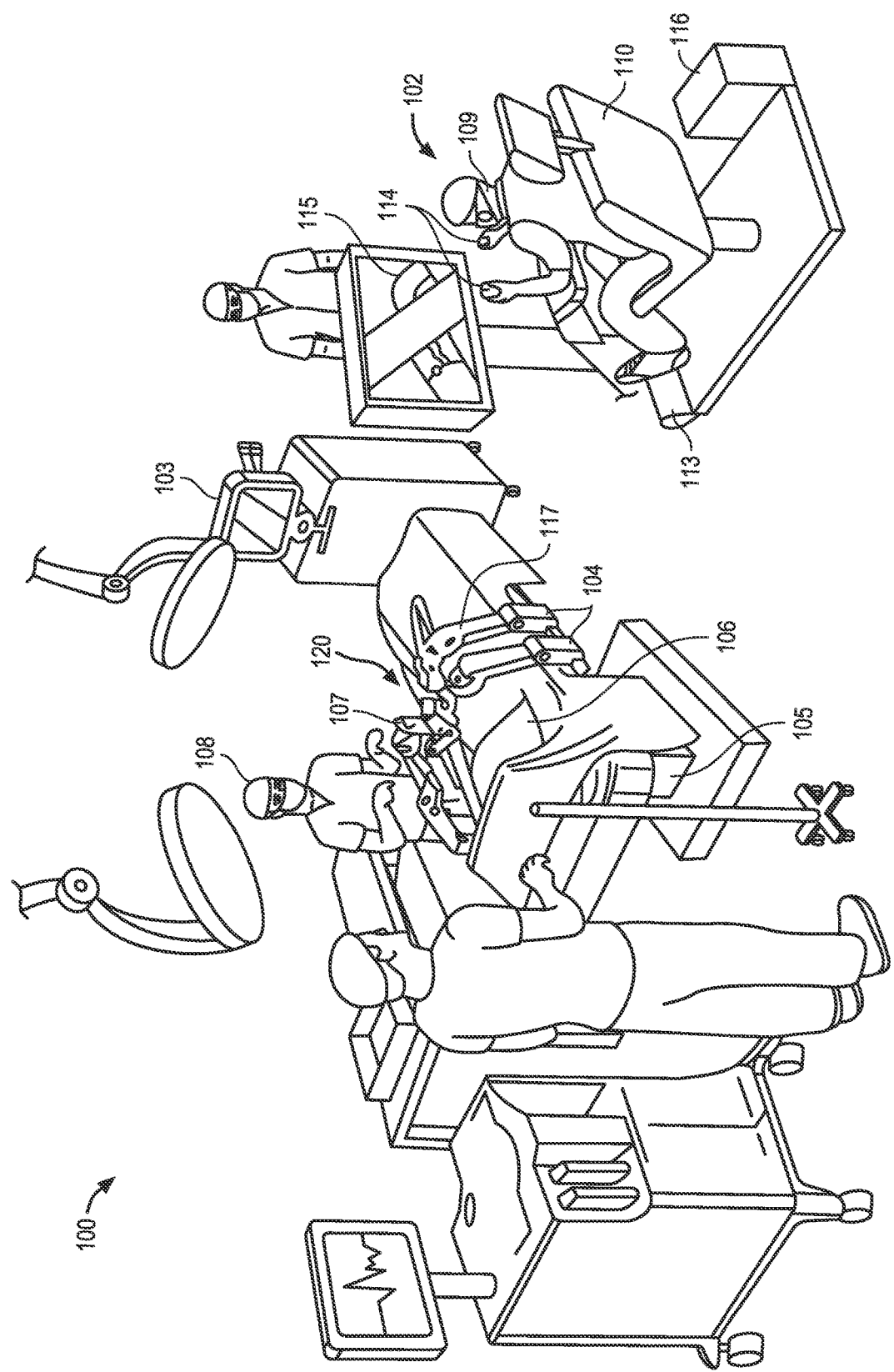
FIG. 1 is an overview schematic of an operating room arrangement with a surgical robotic system.

In various embodiments, description is made with reference to the figures. However, certain embodiments may be practiced without one or more of these specific details, or in combination with other known methods and configurations.

In the following description, numerous specific details are set forth, such as specific configurations, dimensions, and processes, in order to provide a thorough understanding of the embodiments. In other instances, well-known processes and manufacturing techniques have not been described in a particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure. In some aspects, surgical tool 107 may include one or more of an energy tool, a harmonic tool, a stapler, or any other surgical tool or device.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 may be a grasper that can grasp tissue of the patient and/or an energy tool that can emit energy to cut, coagulate, desiccate and/or fulgurate the grasped tissue. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. Teleoperation may be engaged or disengaged based on the user actions. It should be understood that "engaging" the teleoperation mode is intended to refer to an operation in which, for example, a UID or foot pedal that is prevented from controlling the surgical instrument, is transitioned to a mode (e.g., a teleoperation mode) in which it can now control the surgical instrument. On the other hand, disengaging the teleoperation mode is intended to refer to an operation which occurs when the system is in a teleoperation mode, and then transitioned to a mode (non-teleoperation mode) in which the UID or foot pedal can no longer control the surgical instrument. For example, teleoperation mode may be disengaged when the system determines that a detected movement is an unintended action or movement by the user or the user engages in any other action which suggests teleoperation mode should no longer be engaged.

The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site). To create a port for enabling introduction of a surgical instrument into the patient 106, a trocar assembly may be at least partially inserted into the patient through an incision or entry point in the patient (e.g., in the abdominal wall). The trocar assembly may include a cannula or trocar, an obturator, and/or a seal. In some variations, the trocar assembly can include an obturator such as a needle with a sharpened tip for penetrating through a patient's skin. The obturator may be disposed within the lumen of the cannula when being inserted into the patient 106, and then removed from the cannula such that a surgical instrument may be inserted through the lumen of the cannula. Once positioned within the body of the patient 106, the cannula may provide a channel for accessing a body cavity or other site within the patient 106, for example, such that one or more surgical instruments or tools (e.g., an energy tool) can be inserted into a body cavity of the patient 106, as described further herein. It will be understood that the cannula as described herein may be part of a trocar, and can optionally include an obturator or other components.

Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106. In some aspects, the surgical tool grasper may be a surgical stapler or energy tool and the UIDs 114 are used to control the opening or closing of the jaw of the surgical stapler or energy tool as well as the release of staples and/or energy application through the tissue. When the user is finished controlling the surgical tools with the UIDs 114, the user may dock (i.e., store) the UIDs 114 with docking stations or UID holders located on the console 102.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

Figure 2:
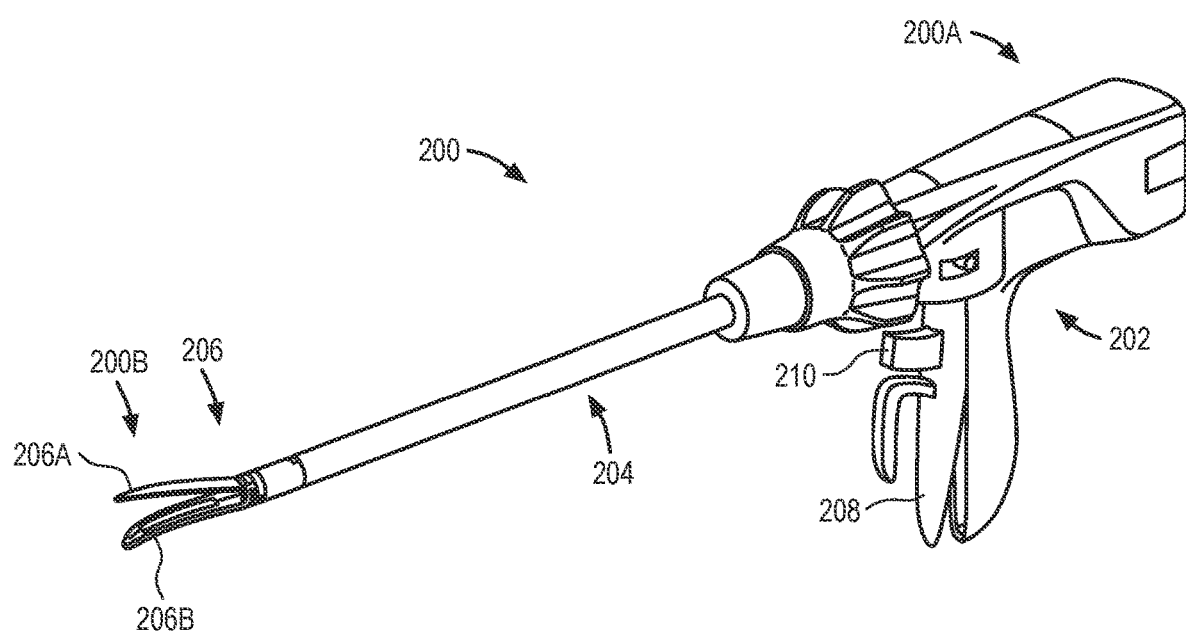
FIG. 2 is a side perspective view of one aspect of surgical tool of a surgical robotic system.

Turning now to FIG. 2, FIG. 2 illustrates a perspective view of one exemplary surgical tool or instrument 200 for a surgical robotic system. Tool 200 may include a proximal end 200A that is held by the user outside of the patient during a surgical procedure and a distal end 200B that is inserted into the patient during a surgical procedure. Tool 200 may include a handle portion 202, a shaft portion 204 and a surgical tool grasper or jaw 206 coupled to the shaft portion 204. The handle portion 202 may include various mechanisms, for example a lever or trigger 208 and actuator button 210, suitable for manipulating the jaw 206 within the patient and controlling an energy application. For example, the lever or trigger 208 may be operable to transition between a closed position causing jaw 206 to clamp onto a tissue and/or otherwise perform a surgical operation (e.g., emission of energy from jaw 206) and an open position in which jaw 206 opens and/or the surgical operation is terminated (e.g., no emission of energy from jaw 206). Representatively, in some aspects, moving lever or trigger 208 toward a closed position (e.g., closer to handle portion 202) will cause the top anvil 206A and bottom anvil 206B of jaw 206 to move closer together. Said another way, this operation decreases the gap or distance between top anvil 206A and bottom anvil 206B so that jaw 206 clamps onto a tissue positioned therein, or the clamping force on the tissue is increased. Conversely, in some aspects, moving lever or trigger 208 toward an open position (e.g., away from handle portion 202) will cause the top anvil 206A and bottom anvil 206B of jaw 206 to move farther apart. Said another way, this operation increases the gap or distance between top anvil 206A and bottom anvil 206B so that a clamping force of the jaw 206 on the tissue positioned therein is decreased, or the tissue is otherwise released from jaw 206. In some aspects, the closing or opening of lever 208 also actuates the energy application, while in other aspects, the energy application may be separately controlled using actuator button 210. For example, lever 208 may be squeezed to close the jaw, or otherwise clamp onto the tissue, and the actuator button 210 may be pressed to cause the energy to be applied from the jaw. In this aspect, releasing of the actuator button 210 may terminate the energy application. The shaft portion 204 may be an elongated portion that connects the handle portion 202 to the jaw 206. The shaft portion 204 may enclose circuitry or other components running from the handle portion 202 to jaw 206 for controlling the jaw 206 and the application of energy. The shaft portion 204 may be used to insert and position the jaw 206 within the patient.

Figure 3:
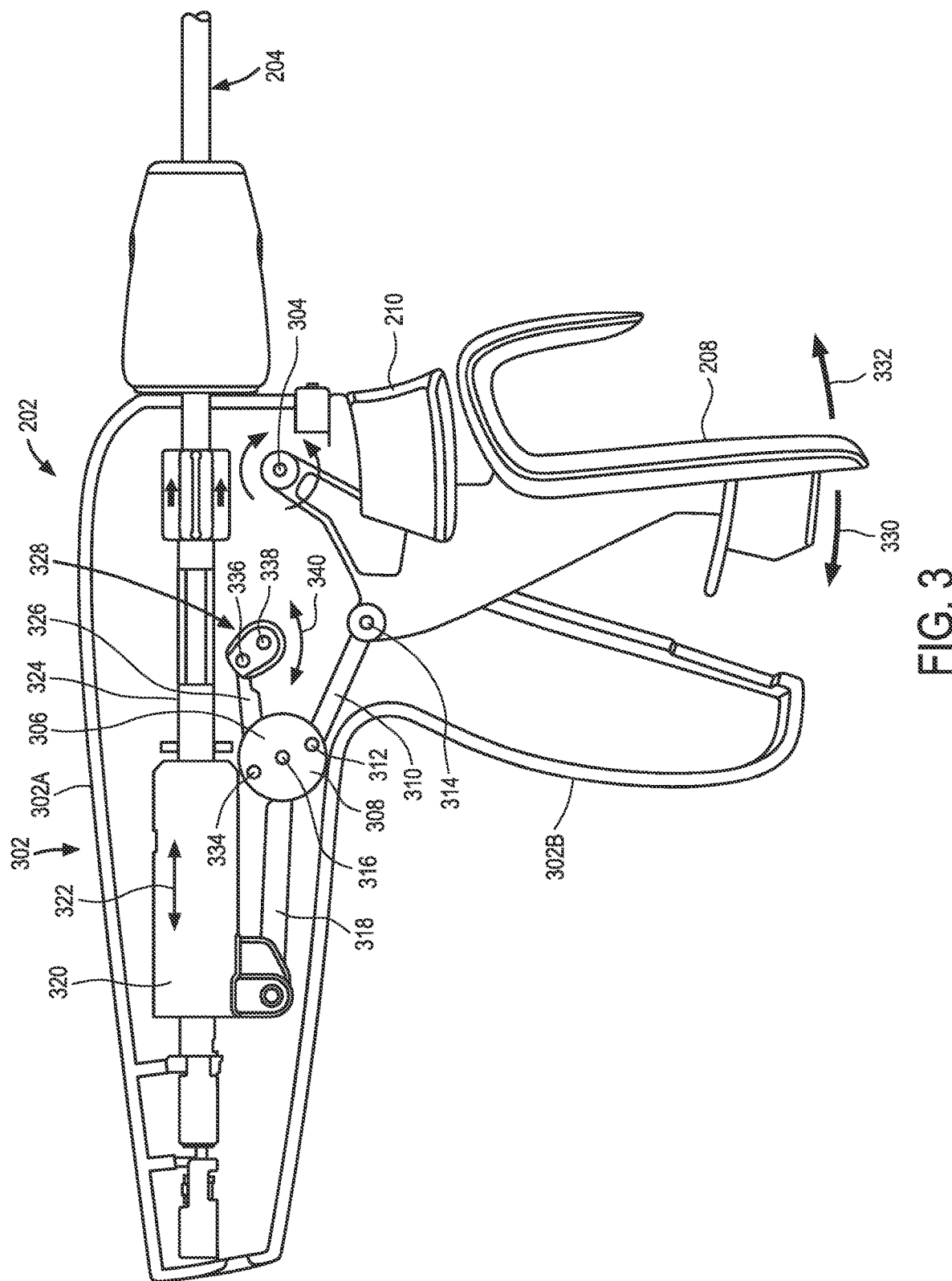
FIG. 3 is a cross-sectional side view of another aspect of a surgical tool of a surgical robotic system having a lever.

A number of representative surgical tools having the combiner mechanism disclosed herein will now be discussed in more detail in reference to FIGS. 3-17. Representatively, FIG. 3 illustrates a cross-sectional side view of the interior components of a surgical tool handle having a combiner mechanism. From this view, it can be seen that handle 202 includes lever 208 in a relatively open position. It should be understood that although not shown in their entirety, handle 202 is coupled to the shaft portion 204 and jaw 206 as previously discussed to form the surgical tool 200. From this view, it can be seen that handle 202 includes a housing 302 that encloses or otherwise supports the various components (e.g., mechanical components, electrical components, or the like) used to operate the surgical tool. The housing 302 may form a body portion 302A and a base portion 302B of handle 202. Body portion 302A may be configured to house most of the electrical and mechanical tool components and be coupled to the shaft portion 204. Base portion 302B may extend from body portion 302A and be configured to rest within, near, or face, a palm of a user's hand when the user is holding the handle 202.

Lever or trigger 208 is movably coupled to housing 302 in front of the base portion 302B such that the user's fingers wrap around, or otherwise contact, lever or trigger 208 when the user grasps handle 202. Lever or trigger 208 may be coupled to housing 302 at pivot point 304 which allows lever or trigger 208 to move relative to base portion 302B. Representatively, lever or trigger 208 may move, pivot or rotate about, pivot point 304 (e.g., a pivot joint or pin), for example, in a clockwise or counterclockwise direction. For example, lever 208 may move in a first direction as illustrated by arrow 330 to a first or closed position in which lever 208 contacts, or is otherwise near, base portion 302B. In some aspects, the first direction may be considered a clockwise direction around pivot point 304, a direction toward base portion 302B or any other direction which moves lever 208 toward base portion 302B to a position considered a closed position. Lever or trigger 208 may also move, pivot or rotate about, pivot point 304 (e.g., a pivot joint or pin), for example, in second direction as illustrated by arrow 332. For example, lever 208 may move in the second direction to a second or open position in which lever 208 is spaced a distance from base portion 302B. In some aspects, the second direction may be considered a counterclockwise direction, a direction away from base portion 302B or any other direction which moves lever 208 away from base portion 302B to a position considered an open position.

As can further be seen from FIG. 3, and the magnified view of portions of the handle in FIGS. 4-8, lever or trigger 208 is also coupled to an actuation combiner mechanism 306 that combines the actuation force input from lever or trigger 208 with a second actuation force input for enhanced tool functionality and/or control. Representatively, actuation combiner mechanism 306 includes a combiner wheel 308 that is rotatably coupled to the handle 202 at a center pivot point 316. The center pivot point 316 may be, for example, a pin or other mechanism that connects combiner wheel 308 to handle 202 and around which combiner wheel 308 can rotate or pivot. Lever or trigger 208 may be coupled to combiner wheel 308 at a pivot point 312 by input link 310. Representatively, input link 310 may have a first end that is connected to combiner wheel 308 at pivot point 312 and a second end that is connected to lever or trigger 208 at a pivot point 314. In this aspect, the movement of the lever or trigger 208 in the direction of arrows 330, 332 will provide an actuation force input to combiner wheel 308. This actuation force input from lever or trigger 208 may, in turn, be transferred by combiner wheel 308 to the actuation combiner output link 318. The actuation combiner output link 318 may be connected at one end to the combiner wheel 308 (e.g., at center pivot point 316). The actuation combiner link 318 may be connected at the other end to yoke assembly 320. Yoke assembly 320 translates in the direction of arrow 322 to drive the movement of the tool grasper or jaw 206 in response to the opening or closing of lever or trigger 208.

Representatively, in some aspects, yoke assembly 320 may be connected to a spring (see e.g., spring 640 of FIG. 6) and circuitry or other components 324 running from handle portion 202 to jaw 206 via shaft portion 204 for controlling the jaw 206 (and the application of energy). For example, in one aspect, moving lever 208 to the closed position (e.g., toward base portion 302B) may generate an actuation input force via input link 310 to actuation combiner mechanism 306. This force, in turn, is transferred to output link 318 which causes the yoke assembly 320 to translate and cause the jaw (not shown) to close, reduce the size of the jaw gap, increase a clamping force on a tissue, or the like, as previously discussed. Conversely, moving lever 208 to the open position (e.g., away from base portion 302B) may generate an actuation input force via input link 310 to actuation combiner mechanism 306. This force, in turn, is transferred to output link 318 which causes the yoke assembly 320 to translate in an opposite direction and cause the jaw (not shown) to open, increase a size of the jaw gap, reduce a clamping force, or the like, as previously discussed.

As can further be seen from this view, actuation combiner mechanism 306 is also connected to another input link 326. Input link 326 generates or produces a second actuation force input. The combiner mechanism 306 combines this second actuation force input of the input link 326 with the actuation force input from the lever 208 to output a combined force via the output link 318. Representatively, in some aspects, the combined ratio of the two inputs from links 310, 326 may be controlled by selecting, or changing, the ratio of the radial distances of the pivot points 312, 334 to the combiner wheel center pivot point 316. Representatively, as can be seen from the magnified view of the combiner mechanism 306 in FIG. 4, the pivot point 334 of input link 326 on combiner wheel 308 has a radial distance (r1) from the center pivot point 316 of combiner wheel 308. In addition, the pivot point 312 of input link 310 on combiner wheel 308 has a radial distance (r2) from the center pivot point 316 of combiner wheel 308. The ratio of these radial distances (r1) and (r2) may be selected, or changed, to achieve a desired combined ratio of the two inputs. Representatively, for input link 310, the combined ratio of the two inputs may be represented as follows: r1/(r1+r2). On the other hand, for input link 326, the combined ratio of the two inputs may be represented as follows: r2/(r1+r2). In this aspect, if the radial distance (r1) for link 326 is selected to be bigger than radial distance (r2) for link 310, the force needed to generate the output will be reduced. In turn, a smaller input force to combiner combiner wheel 308 by link 326 may be necessary (e.g., a preloaded spring coupled to link 326 may be less compressed and produce a smaller force to link 326). When radial distance (r1) and radial distance (r2) are the same, half the actuation force input comes from link 326 and half the actuation force input comes from link 310. In some aspects, the radial distances (r1) or (r2) may be changed by including a slot in the combiner wheel 308 that allows the pivot points 312, 334 (e.g., the pivot point pins) to slide radially along combiner wheel 308 to different positions closer or farther away from center pivot point 316.

In some aspects, input link 326 is connected to an adjustment mechanism or lever 328 that produces an actuation force input that adjusts a position of the combiner wheel and can be used to set a default open position of the lever 208. For example, adjustment lever 328 may be movably (e.g., rotatably) connected to the handle housing 302 (e.g., the body portion 302A) at a pivot point 338 such that it can pivot/rotate in a clockwise or counterclockwise direction as shown by arrow 340. The input link 326 may include one end that is coupled to the combiner wheel 308 at a pivot point 334 and another end that is connected to the adjustment lever 328 at a pivot point 336. In some aspects, adjustment lever 328 may have an elongated shape (e.g., rectangular, teardrop, or the like) and pivot point 336 for input link 326 may be positioned at one end while pivot point 338 for lever 328 is positioned at another end. It is noted that any of the pivot points discussed herein (e.g., pivot points 304, 312, 314, 316, 334, 336, 338) may, for example, be formed by a pin, bolt or other connecting member positioned through the connected components in such a manner that one or more of the components can move about the pint or bolt and relative to one another.

The rotation or pivoting of adjustment lever 328 about pivot point 338 in a counterclockwise direction (e.g., to the left) or clockwise direction (e.g., to the right), pushes or pulls input link 326 to the left or right generating the actuation force input to the combiner wheel 308 from the input link 326. This pushing or pulling on combiner wheel 308 may, in turn, cause the combiner wheel 308 to translate (e.g., move left or right) and/or rotate (e.g., clockwise or counterclockwise) between different positions. The movement of the combiner wheel 308 between these different positions may be used to change a default position of the input links 310, 326 and/or a default opening position of the lever 208 coupled to the input link 310. Representatively, as can be seen more clearly from FIG. 5 in which combiner wheel 308 is omitted and shown in dashed lines so that structures under wheel 308 are more visible, center pivot point 316 is formed by a pin which can translate as shown by arrow 504 within a slot 502 coupled to housing 302. For example, the pin can translate between a first position near end 506 of slot 502 and a second position near end 508 of slot.

The translation of the pin within slot 502 may also cause combiner wheel 308, which is attached to the pin, to translate and/or rotate between different positions. The translation and/or rotation of combiner wheel 308, in turn, changes the default position of the input links 310, 326. For example, as can be seen from FIG. 4, when the pin forming the center pivot point 316 of combiner wheel 308 is closer to the end 506 of slot 502 (e.g., moved to the right), combiner wheel 308 may move to the right and/or rotate causing pivot point 334 and input link 326 to move to the left and pivot point 312 and input link 312 to move to the right and have a first default position. In this aspect, pivot point 334 may be considered to the left of center while pivot point 312 may be considered to the right of center as shown by the diagonal line through the center point 316. Conversely, when the pin forming the center pivot point 316 of combiner wheel 308 is closer to the end 508 of slot 502 (e.g., moved to the left), combiner wheel 308 may move to the left and/or rotate causing pivot point 334 and input link 326 to move to the right and pivot point 312 and input link 310 to move to the left and have a second default position.

Figure 6:
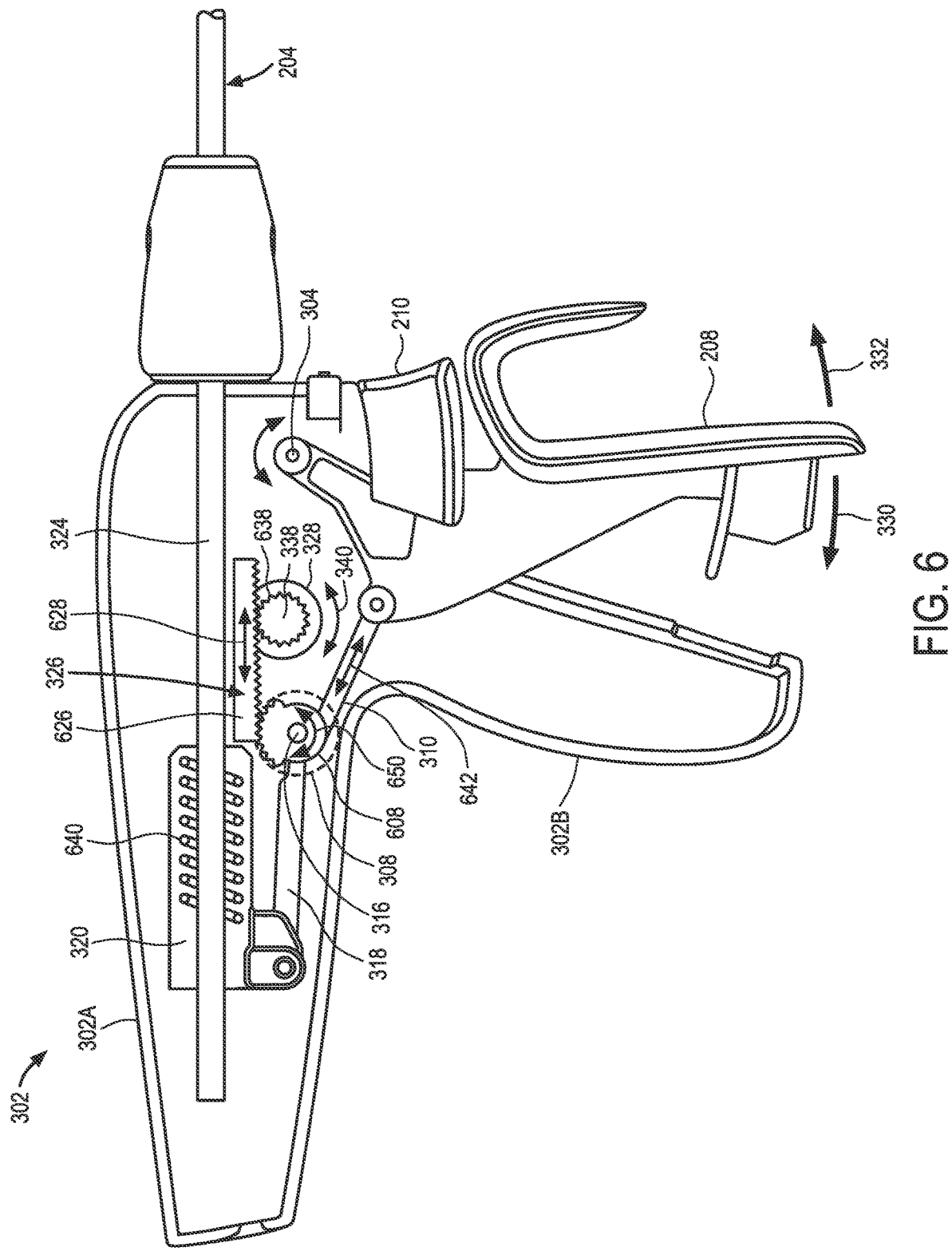
FIG. 6 is a cross-sectional side view of another aspect of a surgical tool of a surgical robotic system having a lever.

One exemplary mechanism including a rack and pinion for driving the movement of pivot point 316 can be seen from FIG. 6. Representatively, as can be seen from FIG. 6, adjustment lever 328 may include a circular gear member 638 (e.g., a pinion) attached to adjustment lever 328 such that rotation of adjustment lever 328 about pivot point 338 drives a rotation of gear member 638. The input link 326 may include a linear gear member 626 (e.g., a rack) that can translate in the direction of arrow 628 (e.g. left or right) and is positioned above, and in contact with, the circular gear member 638. Combiner wheel 308 may further include a circular gear member 608 that rotates about center pivot point 316. The linear gear member 626 may also be positioned above, and in contact with, circular gear member 608. In this aspect, the translation of linear gear member 626 in the direction of arrow 628 also drives, or otherwise causes, a movement of gear members 638 and 608. For example, a movement of adjustment lever 328 in a counterclockwise direction about pivot point 338 as shown by the arrow 340, or to the left, will cause circular gear member 638 to rotate in a counterclockwise direction. This rotation of circular gear member 638 in a counterclockwise direction as shown by the arrow 340 will, in turn, cause linear gear member 626 to translate to the left. This translation of linear gear member 536 to the left will, in turn, cause circular gear member 608 attached to combiner wheel 308 to rotate in a counterclockwise direction about pivot point 316 as shown by arrow 650. Since circular gear member 608 is attached to combiner wheel 308, this will also cause combiner wheel 308 to rotate and/or translate within slot 502 between ends 506, 508. On the other hand, a movement of adjustment lever 328 in a clockwise direction about pivot point 338, or to the right, will cause circular gear member 638 to rotate in a clockwise direction. This rotation of circular gear member 638 in a clockwise direction will, in turn, cause linear gear member 626 to translate to the right. This translation of linear gear member 536 to the right will, in turn, cause circular gear member 608 attached to combiner wheel 308 to rotate in a clockwise direction about pivot point 316 as shown by arrow 650. Since circular gear member 608 is attached to combiner wheel 308, this will also cause combiner wheel 308 to rotate and/or translate within slot 502 between ends 506, 508.

Since both input links 310, 326 are attached to combiner wheel 308, the movement (rotation and/or translation) of combiner wheel 308 will, in turn, change the default position of the links 310, 326. For example, the default position of links 310, 326 could be translated to different staring default positions in the directions shown by the arrows 628, 642. In some aspects, changing the default positions of links 310, 326 may also set a default opening and/or closing position of lever 208. This aspect may help to improve ergonomics in that the default position of lever 208 can be set, or otherwise changed, depending on a size of the user's hand. In still further aspects where the tool is motorized (e.g., mechanism 328 is replaced with a motor), these aspects can be used to allow for a low force closure to be used as a default value, to have a soft clamping force. For example, it is contemplated that once the low force clamp is done, the motor may set the tool to high force just before sealing energy delivery, allowing the motor to handle the hard effort to the final high force clamp.

Figure 7:
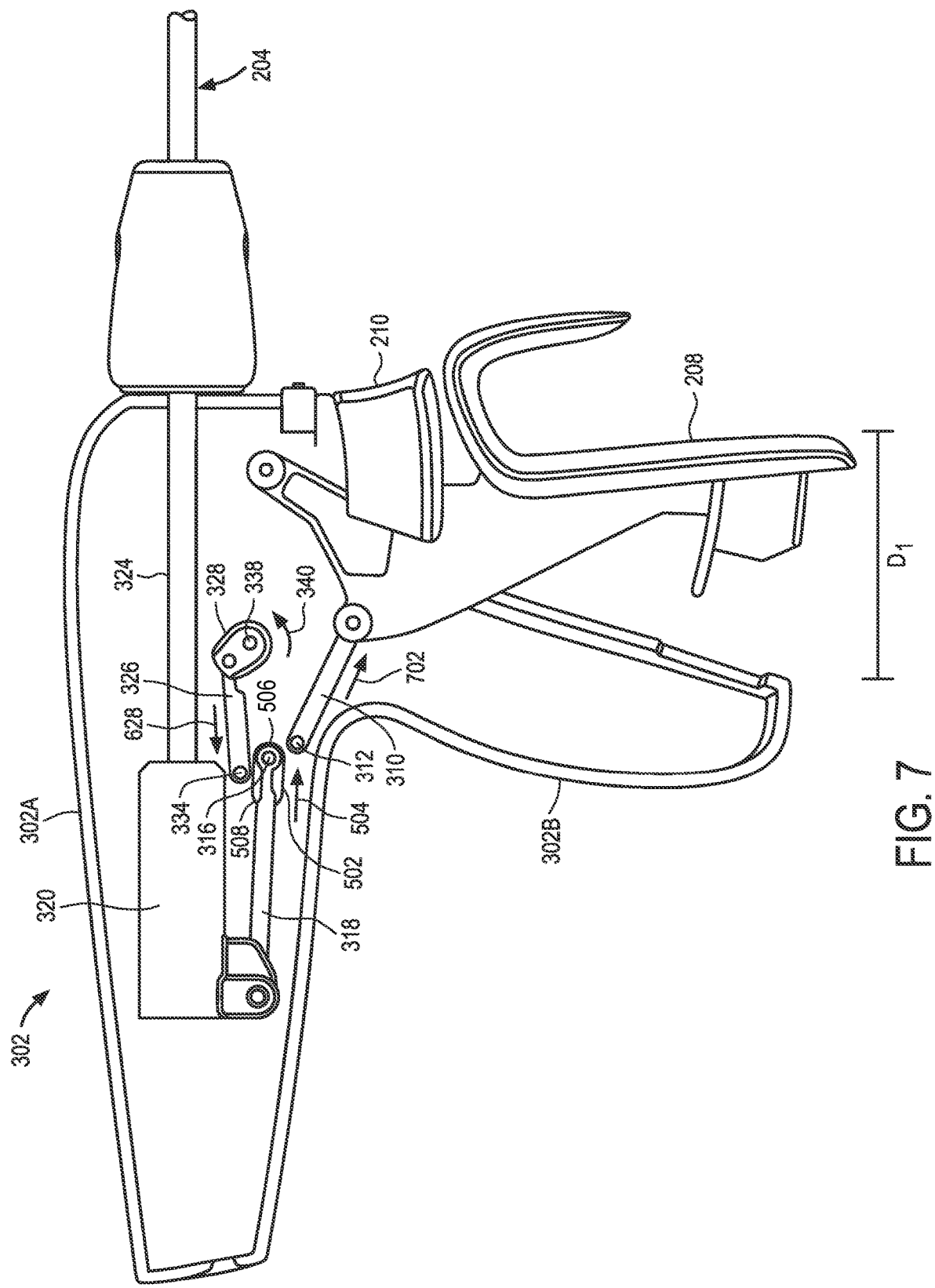
FIG. 7 is a cross-sectional side view of another aspect of a surgical tool of a surgical robotic system having a lever in a first default position.
Figure 8:
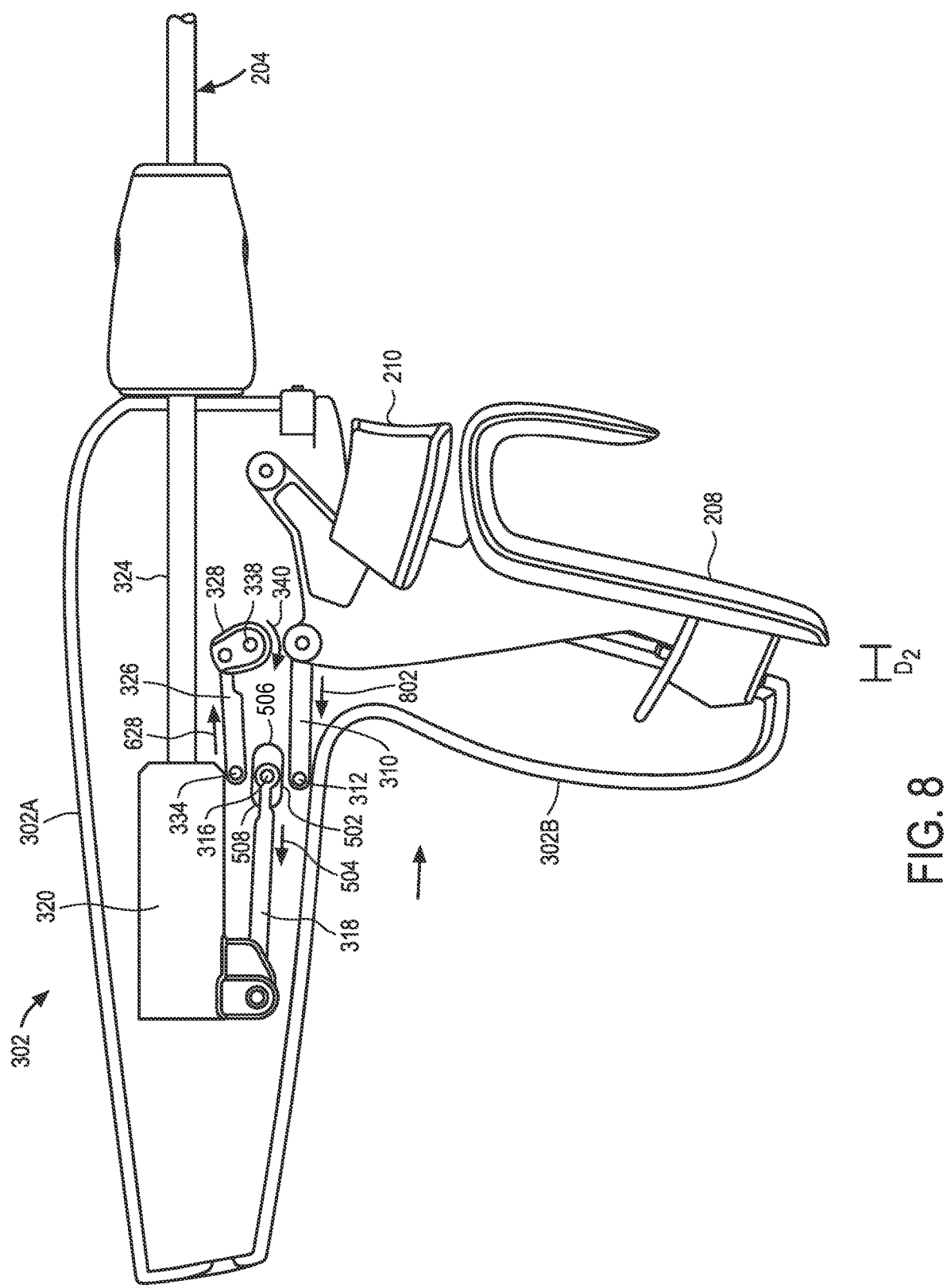
FIG. 8 is a cross-sectional side view of another aspect of a surgical tool of a surgical robotic system having a lever in a second default position.

Referring now in more detail to the ergonomic advantages previously discussed, FIG. 7 and FIG. 8 illustrate setting of the default position for a big opening (e.g., larger hand) and a small opening (e.g., smaller hand), respectively. Representatively, as can be seen from FIG. 7, moving the adjustment lever 328 to the left (e.g., counterclockwise about pivot point 338) causes center pivot point 316 of the combiner wheel to move in the direction of arrow 504 to a position near the right end 506 of slot 502. In addition, this may rotate the combiner wheel in a counterclockwise direction (not shown) about pivot point 338 essentially lengthening input link 326 and pushing input link 310 attached to lever 208 in the direction of arrow 702. Said another way, pivot point 334 of input link 326 moves to the left of center pivot point 316 while pivot point 312 of input link 310 moves to the right of center pivot point 312. This arrangement, in turn, pushes the lever 208 away from the base portion 302B of the handle resulting in a wider or larger default opening position of the lever 208, as illustrated by the distance (D1). This wider or larger default open position (D1) may be more comfortable, or otherwise desired, by user's with relatively large hands. In some aspects, the user may understand that a movement of adjustment lever 328 to the left, or a placement of lever 328 in a left of center position, will set the lever 208 default position to this wider or larger default open position (D1).

On the other hand, as can be seen from FIG. 8, moving the adjustment lever 328 to the right (e.g., clockwise about pivot point 338) causes center pivot point 316 of the combiner wheel to move in the direction of arrow 504 to a position near the left end 508 of slot 502. In addition, this may rotate the combiner wheel in a clockwise direction (not shown) about pivot point 338 essentially shortening input link 326 and pulling input link 310 attached to lever 208 in the direction of arrow 802. Said another way, pivot point 334 of input link 326 and pivot point 312 of input link 310 are essentially vertically aligned with one another, and relative to center pivot point 312. This arrangement, in turn, pulls the lever 208 toward the base portion 302B of the handle resulting in a narrower or smaller default opening position of the lever 208, as illustrated by the distance (D2). In some aspects, the user may understand that a movement of adjustment lever 328 to the more upright position, or a placement of lever 328 in a center position, will set the lever 208 default position to this narrower or smaller default open position (D1). This narrower or smaller default open position (D2) may be more comfortable, or otherwise desired, by user's with relatively small hands.

As can further be understood from the previous description, actuation of each link coupled to the combiner wheel contributes to the movement of the other links. In some aspects, slot 502 may therefore be understood as limiting the degree of movement of the actuation transfer between the links. Representatively, while the output link center pivot point 316 is within the limits of slot 502, any link actuation contributes to the other two links. For example, when the center pivot point 316 is on the right limit of slot 502 (e.g., end 506), pulling actuation on input link 326 will generate actuation transfer only to input link 310. In addition, for a fixed position of adjustment lever 328 only a pushing actuation force on input link 310 will be transferred to input link 326. In this aspect, pulling movements on the input link 326 using adjustment lever 328 will close (or make smaller) the lever 208 default position.

Figure 9:
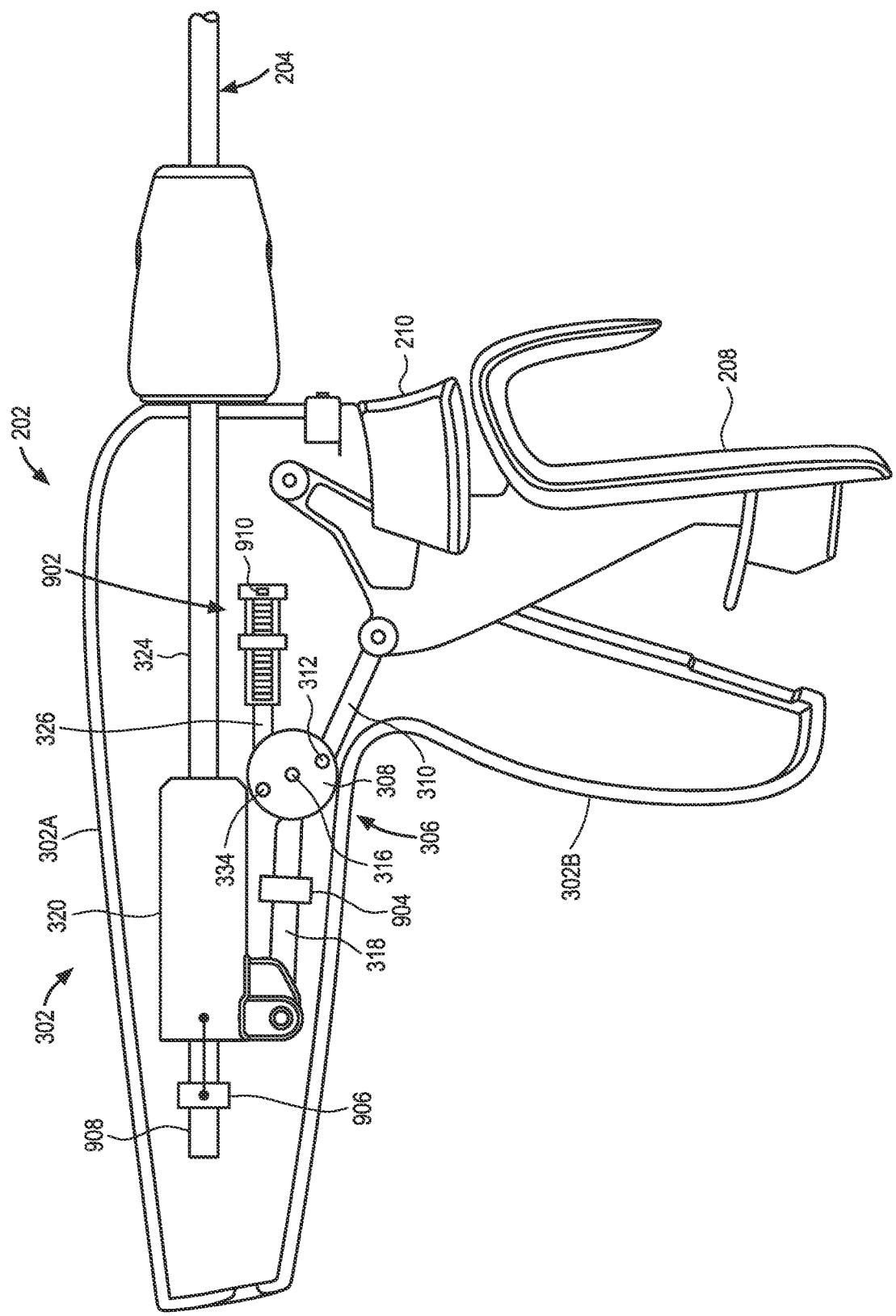
FIG. 9 is a cross-sectional side view of another aspect of a surgical tool of a surgical robotic system.

Referring now to FIG. 9, FIG. 9 illustrates a cross-sectional side view of another aspect of a surgical tool handle having a combiner mechanism. The tool handle 202 includes the same features as the previously discussed handles. For example, handle 202 includes housing 302 defining the handle body portion 302A and base portion 302B, lever 208 connected to the base portion 302B, and yoke 320 connected to circuitry or other components 324 and shaft 204 for controlling the grasper or jaw (not shown). In addition, handle 202 includes a combiner mechanism 306 that couples the handle input link 310 and input link 326 to an output link 318 that outputs the actuation force input by the links 310, 326 to yoke 320. In this aspect, however, input link 326 is connected to a preloaded spring assembly 902. Therefore, in this aspect, the combiner mechanism 306 combines the actuation input force from link 310, which is generated, produced or caused by lever 208, with the actuation input force from link 326, which is generated, produced or caused by the preloaded spring 902. In addition, in some aspects, the preloaded spring 902 may be used to drive the movement of the yoke 320, and the previously discussed yoke spring 640 described in reference to FIG. 6 may be omitted. It should be understood that moving the spring from the position on yoke 320 as discussed in FIG. 6, to input link 326 as shown in FIG. 9, may allow for smaller springs to be used since the force on input link 326 is a ratio of the output actuation force. In addition, this may allow for easier adjustment of the preload force and allow for the possibility to do any such adjustments with low power and small size motors. It is further contemplated that the force generated, produced or caused by preloaded spring 902, or the position of preloaded spring 902 within housing 302, in combination with the input forces from lever 208, may be used to modify, enhance or improve certain functions of tool handle 202.

For example, as further shown in FIG. 9, the tool handle assembly may include a force sensor 904 coupled to output link 318 for measuring the force output to the yoke 320 and/or jaw or grasper. The tool handle assembly may further include a position sensor 906 coupled to yoke 320 for indirectly measuring the position of the jaw or grasper (e.g. jaw or grasper 206 shown in FIG. 2). For example, as previously discussed, the input force from the preloaded spring assembly 902 and the lever 208 contribute to the jaw clamping force and position (e.g., opening or closing the jaw) via the output link 318 connecting to the yoke 320. For example, squeezing the lever 208 to a more closed position or increasing the force output by spring assembly 902, may increase the force driving the movement of the yoke 320. This, in turn, causes the jaw or grasper to close with a greater clamping or sealing force on a tissue. The force sensor 904 is therefore configured to measure this force output by the lever 208 and spring assembly 902 via the output link 318.

Alternatively, it is contemplated that in some configurations, a further sensor 910 may be used to measure the compressed spring length to determine the spring compression level, which can also be used to provide jaw force information. This force information can then be used to determine (e.g., analyzed by a processor associated with the tool) a sealing pressure of the jaw on the tissue positioned therein. In addition, measuring the position of yoke 320 using position sensor 906 allows for the jaw position (e.g., size of the jaw gap) to be determined. For example, movement of the yoke 320 in a first direction may open the jaw or grasper while movement of yoke 320 in a second, opposite, direction may close the jaw or grasper. Thus, the different positions that yoke 320 moves to in the first and second directions may correspond to the size of the jaw gap when in the open and/or closed position. Position sensor 906 may be positioned along rod 908 and connected to the yoke 320 such that position sensor 906 can detect the movement of yoke 320 to different positions. This information from the position sensor, in turn, can then be used to determine the size of the jaw gap. Knowing the sealing pressure or clamping force of the jaw and/or the size of the jaw gap allows for enhanced jaw control and sealing. For example, when performing a sealing operation with energy application, the forces on the jaw can be modified depending on the energy delivery and/or the energy delivery can be increased/decreased depending on the jaw position and/or clamping force. For example, the energy delivery can be increased/decreased depending on whether the jaw is determined to be more open or more closed. Representatively, if based on the position of the yoke 320 by position sensor 906, it is determined that the jaw is less closed, and therefore the tissue is less compressed, the energy delivery may be decreased. On the other hand, if it is determined that the jaw gap is smaller, and therefore the tissue is less compressed, the energy delivery may be increased. In addition, the user can control how much clamping force to apply to the tissue using the jaw depending on where they are at in the energy cycle. For example, the user could apply smaller forces when initially clamping onto the tissue, then larger forces as the energy cycle proceeds.

Figure 10:
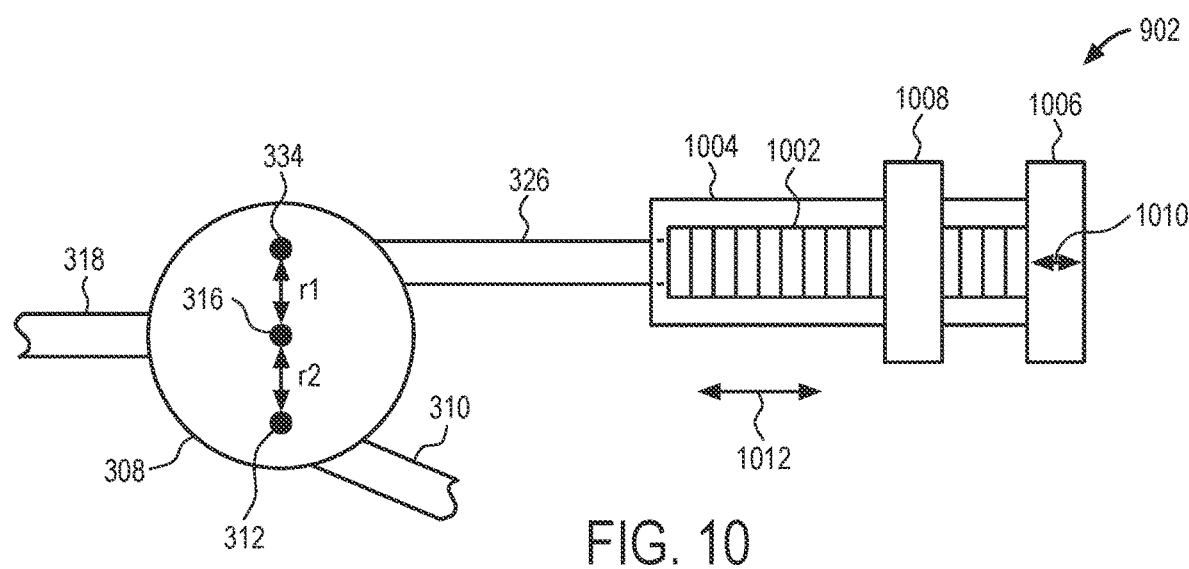
FIG. 10 is a magnified cross-sectional side view of an aspect of the surgical tool of FIG. 9.
Figure 11:
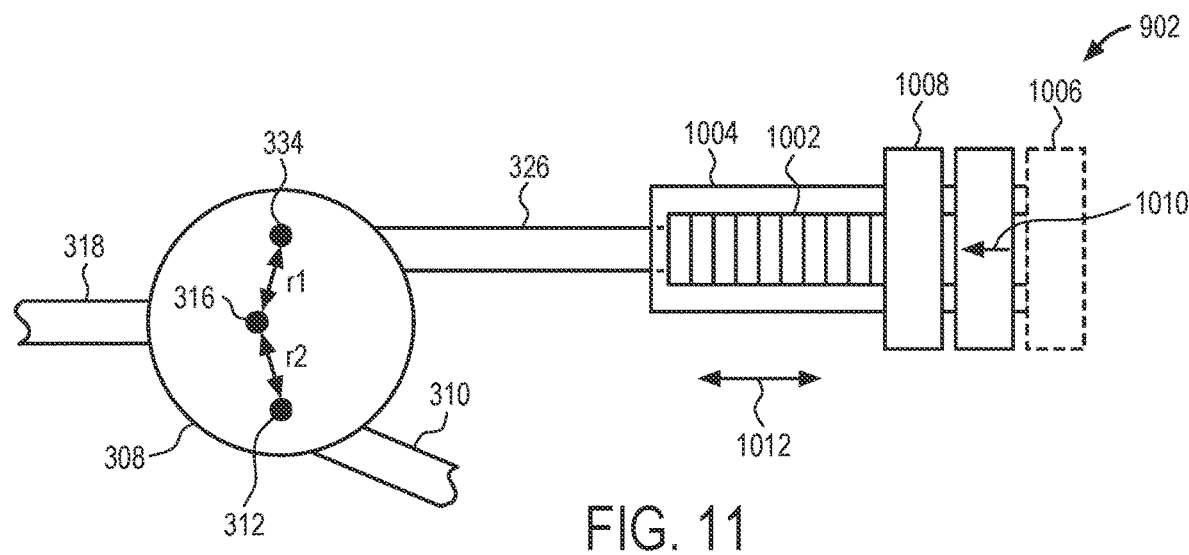
FIG. 11 is a magnified cross-sectional side view of an aspect of the surgical tool of FIG. 9.
Figure 12:
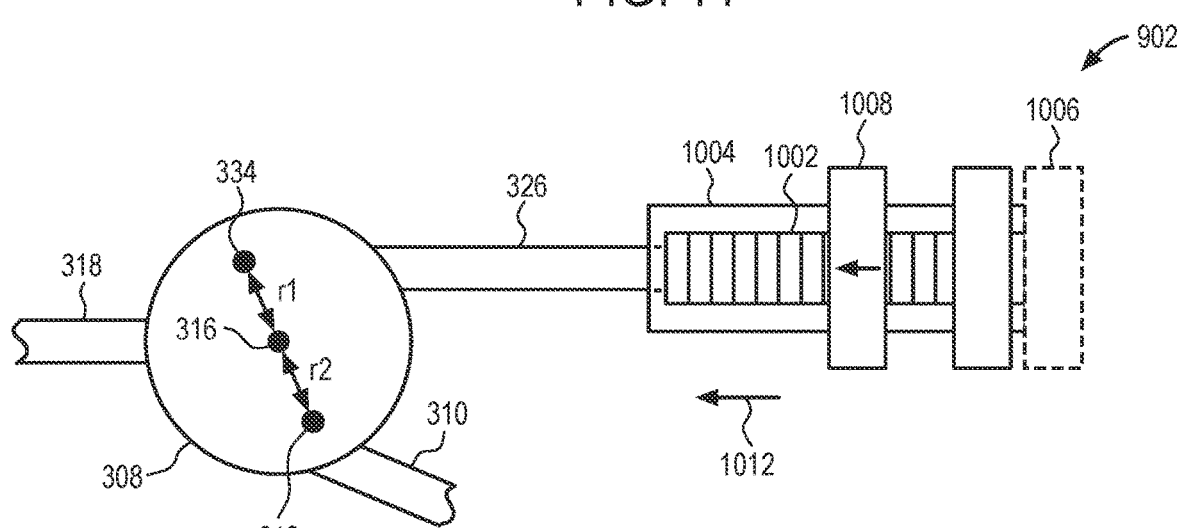
FIG. 12 is a magnified cross-sectional side view of an aspect of the surgical tool of FIG. 9.

The input forces may, for example, be modified by adjusting the force output of the preload spring assembly 902 as will now be discussed in more detail in reference to FIG. 10, FIG. 11 and FIG. 12. FIGS. 10-12 illustrate magnified views of the preloaded spring assembly 902. Representatively, as can be seen from FIG. 10, preloaded spring assembly 902 includes a spring 1002 positioned within a spring housing 1004. The spring 1002 may be connected to the input link 326 so that the force from the spring 1002 provides an actuation input force to the input link 326. Spring housing 1004 may be attached to the handle, for example, the previously discussed handle housing 302. Spring housing 1004 may be any sort of enclosure or other structure capable of containing spring 1002 in a desired location within housing 302. Spring assembly 902 may further include a force adjustment member 1006 and a housing adjustment member 1008 coupled to the housing 1004 and/or spring 1002. Force adjustment member 1006 may be any sort of mechanism that can adjust the force output by spring 1002. For example, in some aspects, spring 1002 may be a compression spring. Force adjustment member 1006 may adjust the force of compression spring 1002 by applying a load that compresses (or condenses) the spring and increases a force output, or by removing the load so that the spring expands and therefore the force output decreases.

Representatively, in some aspects, force adjustment member 1006 may be a threaded nut that is coupled to a complimentary threading about housing 1004 and which can be rotated to move it in the direction of arrow 1010 to compress or expand spring 1002. For example, as illustrated by FIG. 11, when nut 1006 is rotated about housing 1004 in one direction, it translates in the direction of arrow 1010, toward spring 1002, and compresses spring 1002 (or makes it shorter) thereby increasing the force output of spring 1002. Rotating nut 1006 in the opposite direction will translate nut 1006 in the opposite direction (e.g., back to the position shown in FIG. 10), allowing spring 1002 to expand thereby decreasing the force output of spring 1002. In some aspects, since the input force from the spring 1002 contributes to the jaw position control (via the input link 326 connecting to the combiner wheel and the yoke), adjusting the nut 1006 to modify the force can be used to achieve different jaw sealing pressures (or clamping force). For example, where it is desired to increase the jaw sealing pressure (or clamping forces), the compression of the preloaded spring 1002 by force adjustment member 1006 may be increased to increase the force output by spring 1002 to input link 326. This, in turn, increases the combined force output by combiner mechanism to the yoke to drive the clamping of the jaw on a tissue. On the other hand, where it is desired to decrease the jaw sealing pressure (or clamping forces), the compression of the preloaded spring 1002 by force adjustment member 1006 may be reduced to reduce the force output by spring 1002 to input link 326. This, in turn, decreases the combined force output by combiner mechanism to the yoke to drive the clamping of the jaw on a tissue.

Referring now to housing adjustment member 1008, housing adjustment member 1008 may be connected to the housing and may be any sort of mechanism that can adjust the position of housing 1004. Representatively, adjustment member 1008 may translate housing 1004 to different positions, as illustrated by the arrow 1012. Representatively, in some aspects, housing adjustment member 1008 may be a threaded nut that is coupled to a complimentary threading about housing 1004 and which can be rotated to move it in the direction of arrow 1012 to move housing 1004 to the left or to the right. For example, as illustrated by FIG. 12, when nut 1008 is rotated about housing 1004 in one direction, it translates spring housing 1004 in the direction of arrow 1012. Rotating nut 1008 in the opposite direction will translate housing 1004 in the opposite direction (e.g., back to the position shown in FIG. 10). Moving the spring housing 1004 can be used to adjust the handle position and improve ergonomics for the user. Representatively, similar to moving the adjustment lever 328 previously discussed in reference to FIG. 7, moving the spring housing 1004 may change a default position of the combiner wheel 308 and input links 326, 310, which, in turn, changes the default position of the lever connected to input link 310. For example, moving spring housing 1004 in the direction of arrow 1012 (to the left) may cause combiner wheel 308 to rotate counterclockwise about center point 316. The movement of combiner wheel 308 causes the pivot point 334 of input link 326 to move to the left of the combiner center pivot point 316 and causes pivot point 312 to move to the right of the combiner center pivot point 316 as shown in FIG. 12. This essentially lengthens input link 326 and pushes input link 310 away from combiner wheel 308, which, in turn, pushes the lever 208 connected to link 310 away from the handle base portion. This results in a wider or larger default opening position of the lever 208, similar to using the adjustment lever 328 discussed in FIG. 7.

Figure 4:
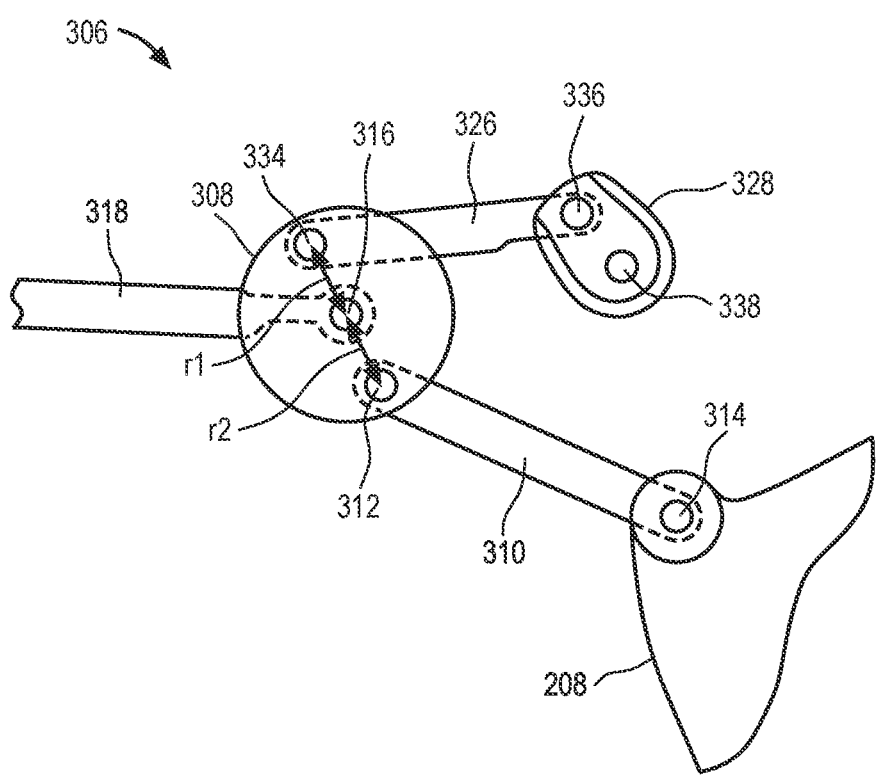
FIG. 4 is a magnified cross-sectional side view of an aspect of the surgical tool of FIG. 3.
Figure 5:
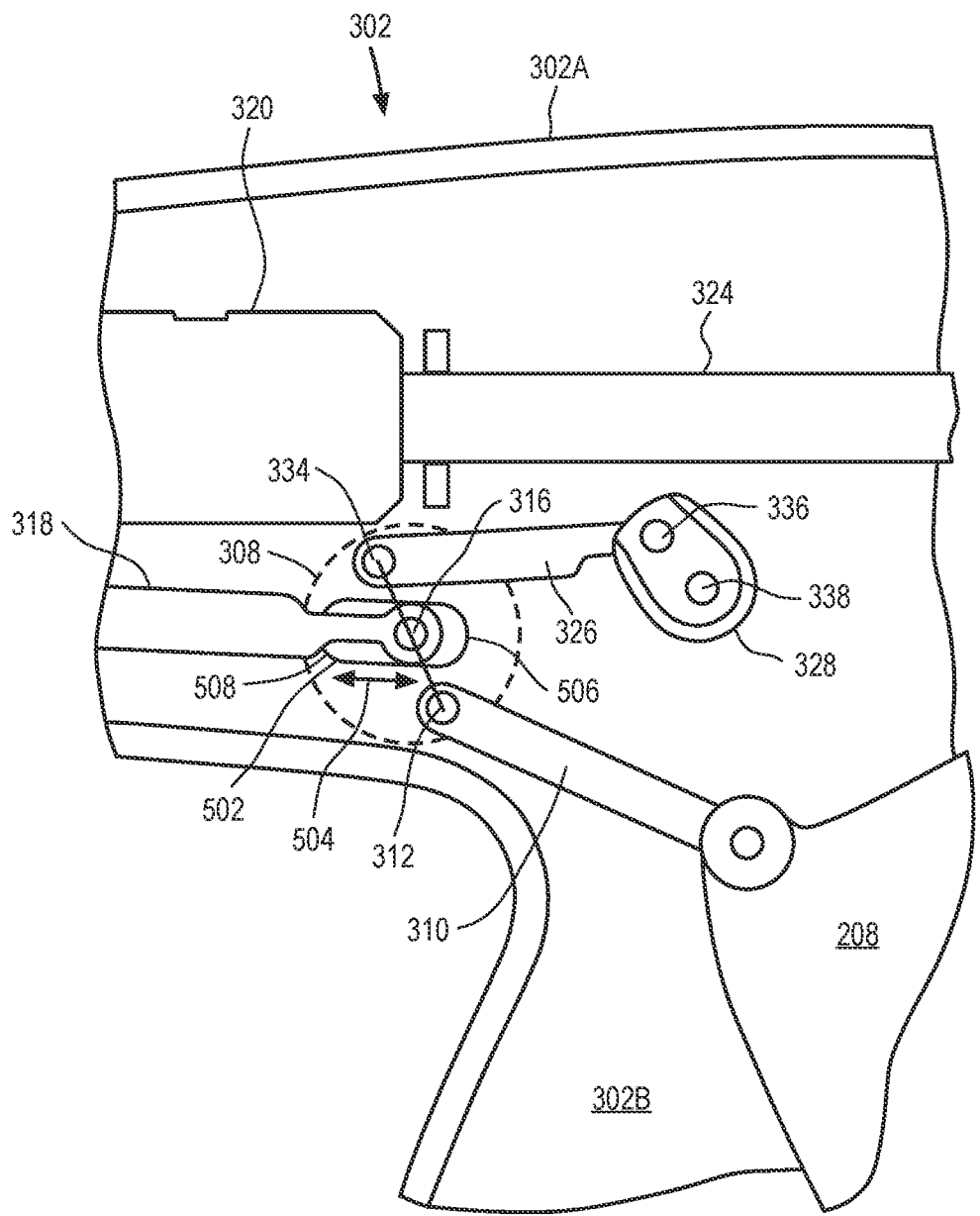
FIG. 5 is a magnified cross-sectional side view of an aspect of the surgical tool of FIG. 3.

In addition, as previously discussed in reference to FIG. 4, the ratio of the radial distances (r1) and (r2) of pivot points 334, 312 to center pivot point 316 of combiner wheel 308 may also impact the preloaded spring force needed to generate the desired output. For example, if the radial distance (r1) for link 326 is selected to be bigger than radial distance (r2) for link 310, the force needed to generate the output is reduced or less. Accordingly, a smaller preloaded spring force may be necessary to generate the output. In this aspect, the compression of preloaded spring 1002 by force adjustment member 1006 may be reduced, which in turn reduces the force output by spring 1002. Alternatively, where the ratio of the radial distances (r1) and (r2) is selected to require a higher force input from preloaded spring 1002, the adjustment member 1006 may be adjusted along the housing to increase the compression of preloaded spring 1002. It should further be understood that although an adjustable preloaded spring 1002 which can be adjusted to modify the force is described, a fixed spring in which the force is not adjustable is also contemplated. Where a fixed preloaded spring is used, the radial distances (r1) and (r2) of the pivot points 334, 312 on combiner wheel 308 may be modified or changed to adjust, or otherwise achieve, the desired force output, instead of changing the compression of the preloaded spring.

Figure 13:
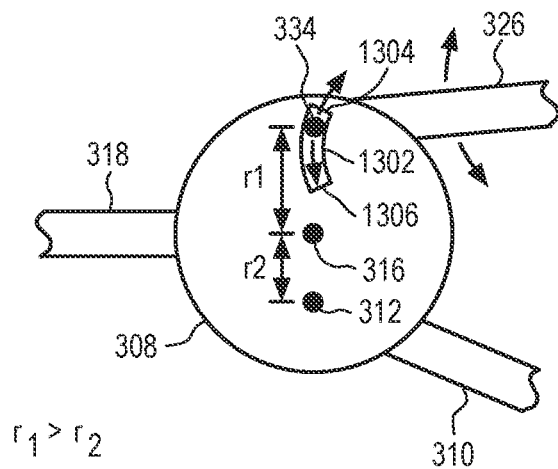
FIG. 13 is a magnified cross-sectional side view of an aspect of the surgical tool of FIG. 9.
Figure 14:
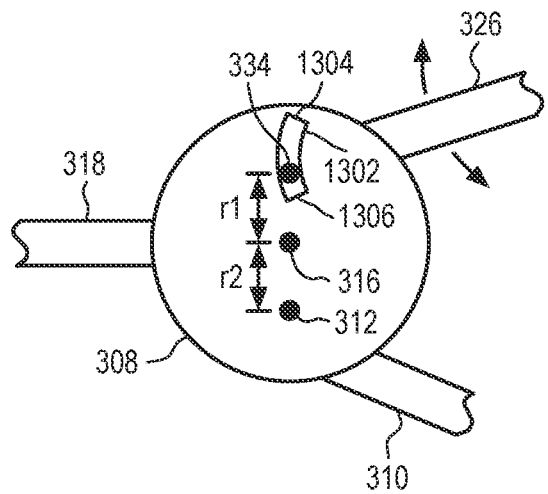
FIG. 14 is a magnified cross-sectional side view of an aspect of the surgical tool of FIG. 9.
Figure 15:
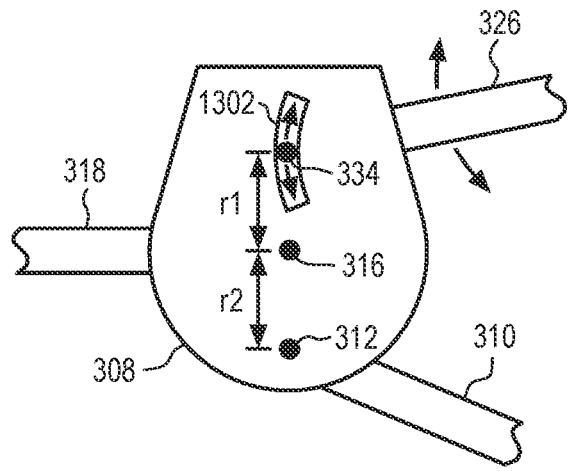
FIG. 15 is a magnified cross-sectional side view of an aspect of the surgical tool of FIG. 9.

Representatively, as illustrated by FIGS. 13-15, the pin forming pivot point 334 may be positioned within an adjustment slot 1302 that runs in a substantially radial direction outward from center pivot point 316. In some aspects, slot 1302 may have a slight curve or bend, or may be relatively straight. To set or change the radial distance (r1), the user may adjust the pin forming pivot point 334 in the direction of the arrows within slot 1302 to any number of positions between the ends 1304, 1306. The adjustment of the pin forming pivot point 334 within slot 1302 further adjusts the position of input link 326 relative to wheel 308 and input link 310. For example, as shown in FIG. 13, when the pin forming pivot point 334 is near the most radially outward end 1304 of slot 1302, the radial distance (r1) of pivot point 334 is greater than the radial distance (r2) of pivot point 312 (e.g., r1>r2). On the other hand, as shown in FIG. 14, when the pin forming pivot point 334 is moved toward the most radially inward end 1306 of slot 1302, the radial distance (r1) of pivot point 334 is substantially equal to the radial distance (r2) of pivot point 312 (e.g., r1=r2). Although not shown, it should be understood that if the pin forming pivot point 334 were moved all the way to the end 1306 of slot 1302, the radial distance (r1) of pivot point 334 may be less than the radial distance (r2) of pivot point 312 (e.g., r1<r2). The pin forming pivot point 334 may be manually adjusted by the user, for example by a knob or other mechanism coupled to the pin and extending from the handle that the user can manually manipulate. In other aspects, the adjustment may be automated, such as by a motor that drives the pin movement and which may be electrically connected to a button or other mechanism the user can press to actuate the movement of the pin. While combiner wheel 308 is shown in the previous configurations having a circular shape, it is contemplated that in other aspects, combiner wheel 308 may have an elongated shape as shown in FIG. 15. For example, combiner wheel 308 may have a tear drop like shape with slot 1302 formed near the narrowest end 1502 of the wheel 308 to accommodate adjustment of the pin forming pivot point 334 to achieve different radial distances (r1) as previously discussed.

Figure 16:
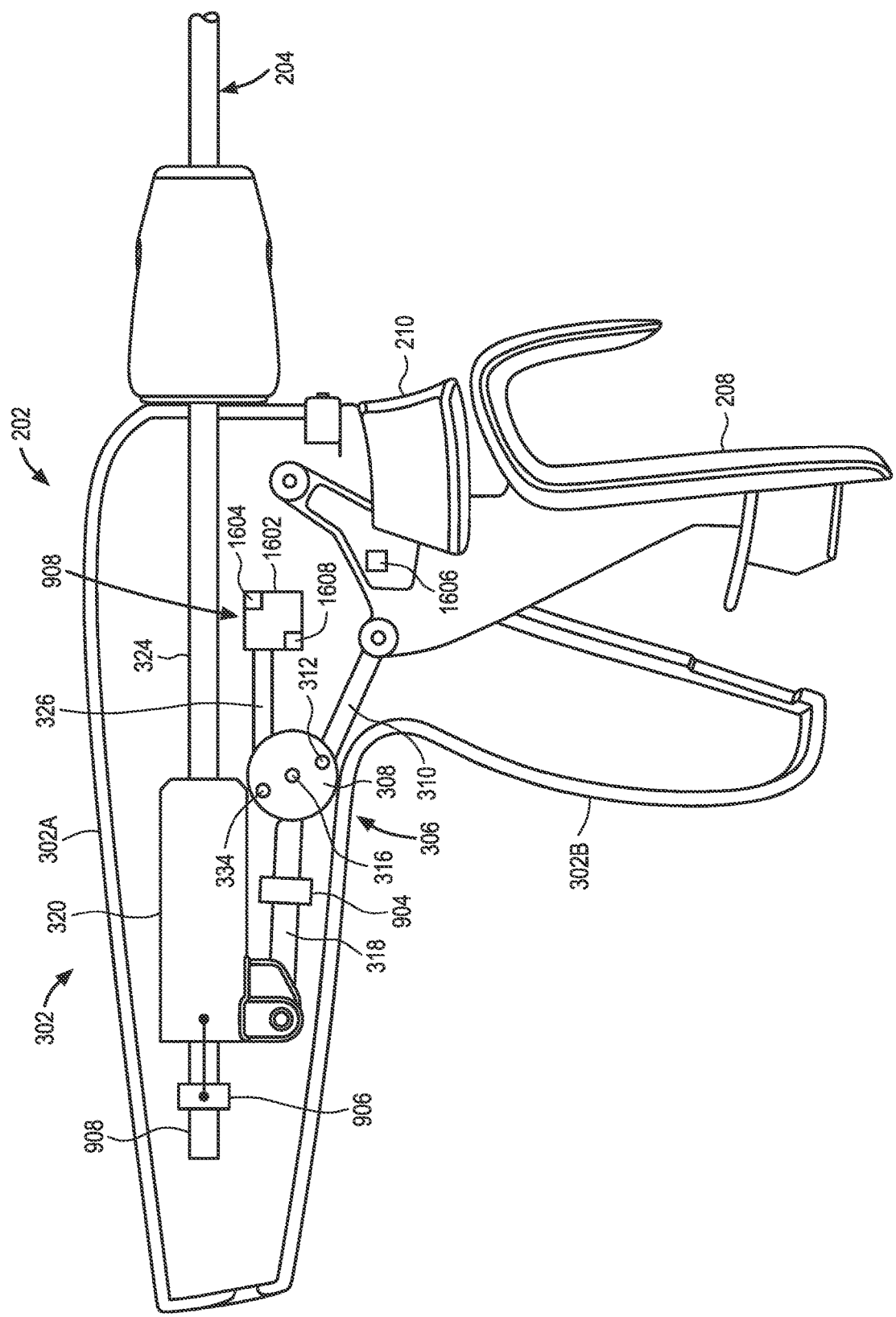
FIG. 16 is a cross-sectional side view of another aspect of a surgical tool of a surgical robotic system.

Referring now to FIG. 16, FIG. 16 illustrates a cross-sectional side view of a tool handle including a motor. Tool handle 202 may be similar to the previously discussed tool handles, except in this configuration, tool handle 202 includes a motor 1602 coupled to the input link 326. Representatively, tool handle 202 includes a housing 302 that forms a body portion 302A and base portion 302B that enclose the handle components, and which is coupled to the tool shaft 204 extending from the handle to the tool grasper or jaw. Lever 208 for controlling the tool grasper or jaw is further coupled to the handle housing 302, near the body portion 302B. Lever 208 is further connected to combiner wheel 308 of combiner mechanism 306 by input link 310. Combiner wheel 308 connects input link 310 to input link 326 and combines the input force from both links 310, 326 to output link 318 to yoke 320. In this configuration, however, input link 326 is connected to a motor 1602 instead of a preloaded spring. In this aspect, the tool handle may be considered automated, instead of manual, and/or many of the previously discussed functionalities may be automated. Motor 1602 may be any sort of motor suitable for providing the desired force input, for example, an N20 motor. In addition, handle may further include a number of sensors 904, 906, 1604, 1606 to detect position, force input/output, etc. of various handle components as previously discussed. For example, the tool handle may include force sensor 904 and/or position sensor 906 as previously discussed. In addition, in some aspects, tool handle may further include a sensor 1604 coupled to the motor 1602 to detect or determine the jaw position and/or a sensor 1606 couple to lever 208 to detect or determine, for example, a position of lever 208. One or more of sensors 1604, 1606 may, in some aspects, be encoders that detect the jaw and/or lever movements and output a corresponding electrical signal that can be used to determine the position of the jaw and/or lever. For example, encoder 1604 coupled to the motor 1602 may indicate a position of motor 1602, which can be used to determine how much the yoke 320 moves, and in turn, how much the jaw is opening or has been opened (e.g., the size of the jaw gap). In some aspects, where motor 1602 includes encoder 1604 to detect or determine the jaw position (e.g., jaw gap size), the position sensor 906 coupled to the yoke 320 may be omitted.

Motor 1602, in combination with the information measured by sensors 904, 906, 1604 and/or 1606, may provide, generate or otherwise produce the actuation force input to input link 326, which is combined with the actuation force input of input link 310 by combiner wheel 308 to provide enhanced functionality and/or additional functions to tool 202. For example, motor 1602 may be used instead of a preloaded spring to automate the tool handle while still providing many of the same enhanced and/or new functionalities as previously discussed, for example, improved sealing, tissue property identification, motor sealing, improved ergonomics, jaw control, overstuffed jaw detection, assisted lever closure, user adjustable sealing force, jaw gap and force measurements. Representatively, the combination of the jaw gap and force data as previously discussed, can be used to detect an overstuffed jaw condition, determine proper sealing parameters, an abnormal sealing sequence, or other functions. Still further, the motor control loop or energy delivery can be closed on jaw pressure or forces data to optimize sealing procedures.

For example, motor 1602 may augment a functionality of lever 208 to provide fine jaw movements and improved jaw control. Representatively, as previously discussed, sensor 1606 may be an encoder that can be used to indicate a movement or position of lever 208, for example, how much the lever 208 is closing or opening (e.g., an opening position distance D1, D2 or any position/distance in between). In addition, encoder 1604 coupled to motor 1602 determines the movement of the motor 1602. The motor 1602 can therefore be controlled to increase or augment the output of the lever 208, or decrease the output of the lever 208. For example, where larger movements of the jaw are desired, the motor 1602 may output a greater force in the same direction as the lever 208, which in turn, causes yoke 320 to move faster, and cause a larger movement of the jaw for a given lever movement. On the other hand, where finer movements are desired, the motor 1602 force output may be in an opposite direction to the lever force output, which in turn, causes yoke 320 to move more slowly. In this aspect, the motor actuation can be used to compliment the manual lever actuation to provide more controlled and/or fine jaw movements as desired.

In still further aspects, motor 1602 can help to provide motorized dynamic and/or variable jaw force and jaw gap control during tissue sealing. This functionality may be similar to the jaw force control previously discussed in reference to the preloaded spring configuration of FIG. 8, except that in this configuration, the jaw force control is motorized (e.g., adjusted using the motor) instead of manual (e.g., adjusted by manually modifying the preloaded spring force). In particular, as previously discussed, when doing sealing, it may be desirable to control one or both of the forces on the jaw and/or the energy delivery relative to one another. For example, the user may wish to deliver more or less energy depending on a size of the jaw opening. Representatively, if based on the position of the yoke 320 by sensor 906 or 904, it is determined that the jaw is less closed, and therefore the tissue is less compressed, the energy delivery may be decreased. On the other hand, if it is determined that the jaw gap is smaller, and therefore the tissue is less compressed, the energy delivery may be increased. In addition, the user may use the motor 1602 to control how much clamping force to apply to the tissue using the jaw depending on where they are at in the energy cycle. For example, the user could reduce the motor output to produce smaller forces when initially clamping onto the tissue, then increase the motor output to produce larger forces as the energy cycle proceeds.

In addition, motor 1602 can be used to provide micro-modulation or dithering during a surgical procedure. Representatively, in some aspects, the movement of the yoke and/or the opening or closing of the jaw may be subject to frictional forces that may ultimately reduce performance. For example, if there are frictional forces opposing the force output used to drive the movement of the jaw, the force applied to the jaw may actually be reduced. Introducing micro modulation (e.g., micro vibrations) to the components used to drive these actions can help to reduce the frictional forces thus resulting in an increased force output or driving force on the jaw. In some aspects, these micro vibrations may be output by an actuator 1608 that is part of, or otherwise associated with motor 1602, and which is operable to generate a micro vibration that can be output by motor 1602. The micro modulation produced from motor 1602 feeds into the combiner mechanism 308, which in turn, introduces the micro modulation into the output link 318 so that it is realized in the force output. In addition, the micro modulation information can be used to provide real time tissue mechanical characteristics information, for example, information regarding tissue stiffness, tissue relaxation or the like. Still further, micro modulation can be used to get a more efficient tissue compression and reduce final gap with same maximum forces applied as in a non-modulated compression.

Figure 17:
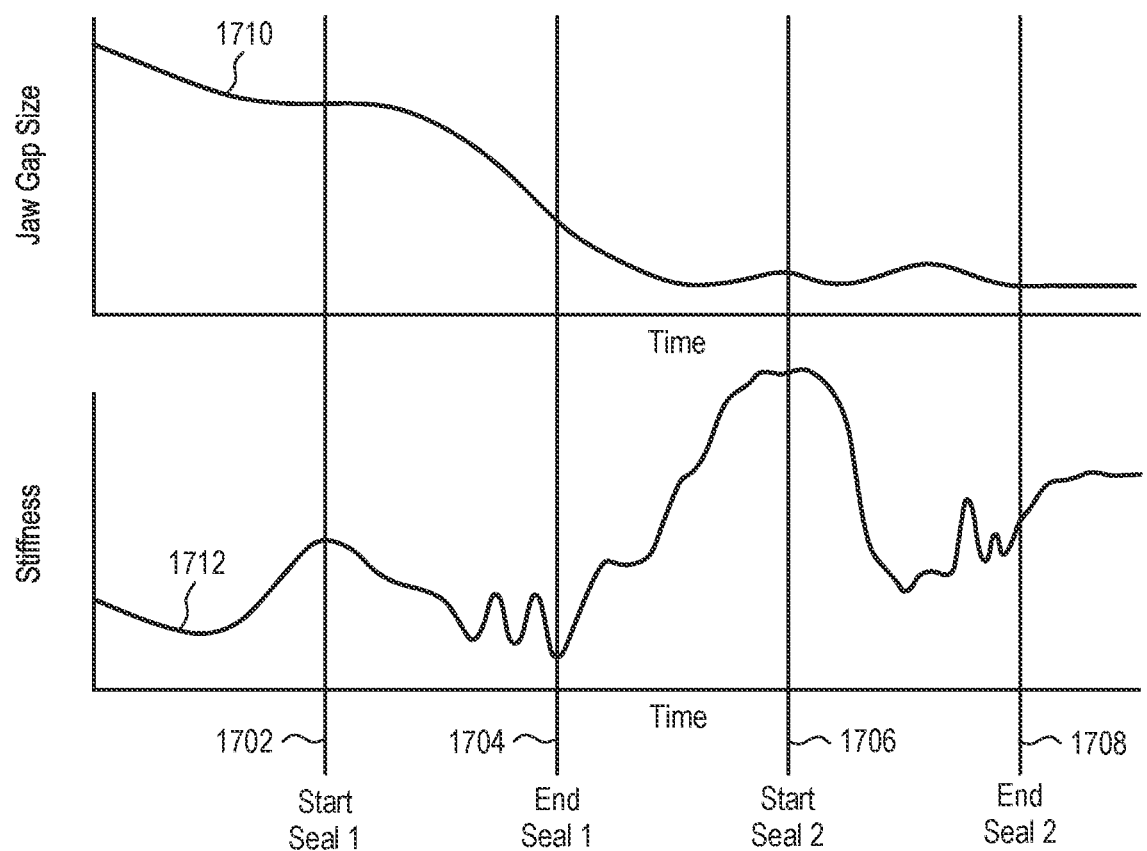
FIG. 17 illustrates a graph comparing jaw gap size of a jaw of the surgical tool and tissue stiffness.

Representatively, FIG. 17 illustrates a graph comparing jaw gap size and tissue stiffness, which can be determined using the micro modulation forces. For example, vertical lines 1702, 1706 represent when the user starts the seal or applies energy, and vertical lines 1704 and 1708 represent when the user ends the seal or terminates energy application. As can be seen from line 1710 of the top graph representing jaw gap size over time, which as previously discussed can be determined using the encoder coupled to the motor, the jaw gap size decreases between the time the user starts the seal and when the user ends the seal. In addition, it can be seen that there is a more significant decrease during the first sealing operation (e.g., between lines 1702 and 1704) than the second sealing operation (e.g., between lines 1706 and 1708). The clamping force, however, is constant therefore the decreasing jaw gap size is a result of the tissue stiffness characteristics changing as the energy is applied. Using this information relating to the variation in jaw gap size along with the micro modulation force information, the changes in stiffness can be illustrated as shown by line 1712 of the bottom graph. Representatively, the stiffness can be measured as a ratio of the peak to peak micro modulation forces divided by the peak to peak variation of the jaw gap size. This ratio can be measured in real time because the micro modulation forces are continuously monitored resulting in real time tissue stiffness or characteristics measurements. From line 1712 of this graph, it can be understood that the stiffness has some variation during a first sealing operation (e.g., the period between lines 1702 and 1704). When the first sealing operation is done, it can be seen from line 1712 that the stiffness begins to rise. Once the second seal starts, as illustrated by vertical line 1706, the stiffness begins to decrease again during the second sealing operation (e.g., the period between lines 1706 and 1708). This information relating to the tissue stiffness and/or relaxation can be used to achieve a more efficient tissue compression and/or sealing operations. For example, knowing the tissue properties such as stiffness and/or relaxation in real time can help identify the different types of tissues during a sealing operation and therefore when to apply more/less clamping forces and/or energy, and to monitor sealing cycles.

Still further, it is contemplated that any of the mechanisms previously discussed in reference to FIGS. 13-15 may further be used in combination with the motor to change or modify the ratio of the radial distances (r1) and (r2) of pivot points 334, 312 to center pivot point 316 of combiner wheel 308 to modify the force needed to generate the desired output. For example, if the radial distance (r1) for link 326 is selected to be bigger than radial distance (r2) for link 310, the motor force needed to generate the output is reduced or less. Accordingly, a smaller motor output force may be necessary to generate the output. Alternatively, where the ratio of the radial distances (r1) and (r2) is selected to require a higher force input, the force output by motor 1602 may be increased.

In still further aspects, it is contemplated that any of the previously discussed tool configurations (e.g., manual or motorized) may have a haptic feedback mechanism. Representatively, it is contemplated that in some aspects the movement of the yoke can present a haptic output (e.g., force, vibration or motion) to the lever 208 that can be felt by the user when using the tool 200. Representatively, in some aspects, when lever 208 is moved by the user (e.g., squeezed or released) it may cause the yoke to move, and this movement of the yoke can be felt as a vibration, resistance feedback or other tactile signal on the lever 208 by the user's hand. This haptic output may indicate to the user that, for example, the jaw is moving, closing, clamping, cutting, applying energy or the like on a tissue, or that these operations are being terminated. In this way, the tool allows the user to feel like they are working directly on the patient even if they are remote to the patient.

Figure 18:
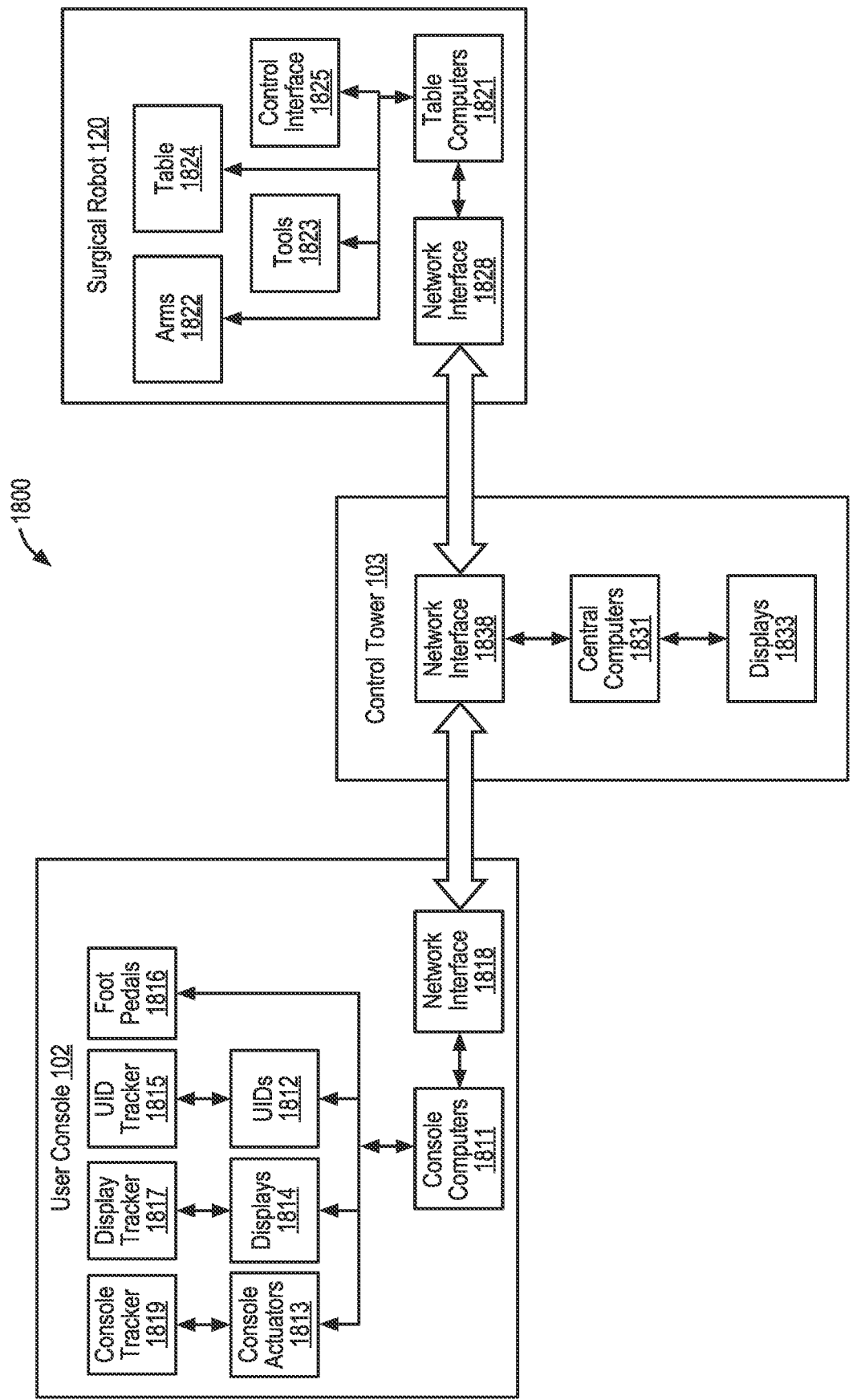
FIG. 18 is a block diagram of a computer portion of a surgical robotic system including an energy tool, in accordance with an aspect of the disclosure.

FIG. 18 is a block diagram of a computer portion of a surgical robotic system, which is operable to implement any one or more of the previously discussed operations. The exemplary surgical robotic system 1800 may include a user console 102, a surgical robot 120, and a control tower 103. The surgical robotic system 1100 may include other or additional hardware components; thus, the diagram is provided by way of example and not a limitation to the system architecture.

As described above, the user console 102 may include console computers 1811, one or more UIDs 1812, console actuators 1813, displays 1814, foot pedals 1816 and a network interface 1818. In addition, user console 102 may include a number of components, for example, a UID tracker(s) 1815, a display tracker(s) 1817 and a console tracker(s) 1819, for detecting various surgical conditions required for operation of the system (e.g., UID orientation, orientation of the surgeon relative to the display, orientation the console seat, etc.). It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 1813 based on user input or stored configurations by the console computers 1811. The user may perform robot-assisted surgeries by controlling the surgical robot 120 using one or more master UIDs 1812 and foot pedals 1816. Positions and orientations of the UIDs 1812 are continuously tracked by the UID tracker 1815, and status changes are recorded by the console computers 1811 as user input and dispatched to the control tower 103 via the network interface 1818. Real-time surgical video of patient anatomy, instrumentation, and relevant software apps can be presented to the user on the high resolution 3D displays 1814 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 18, the control tower 103 may include central computers 1831 including at least a visualization computer, a control computer, and an auxiliary computer, various displays 1833 including a team display and a nurse display, and a network interface 1838 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an operating table 1824 with a plurality of integrated robotic arms 1822 that can be positioned over the target patient anatomy. An energy tool 1823 can be attached to or detached from the distal ends of the arms 1822, enabling the surgeon to perform various surgical procedures. The energy tool 1823 may be any one or more of the energy tools as previously discussed in reference to FIG. 2-FIG. 17. The surgical robot 120 may also comprise control interface 1825 for manual or automated control of the arms 1822, table 1824, and tools 1823. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 1822 includes four arms mounted on both sides of the operating table 1824, with two arms on each side. For certain surgical procedures, an arm mounted on one side of the table can be positioned on the other side of the table by stretching out and crossing over under the table and arms mounted on the other side, resulting in a total of three arms positioned on the same side of the table 1824. The surgical tool can also comprise table computers 1821 and a network interface 1828, which can place the surgical robot 120 in communication with the control tower 103.

The foregoing description, for purposes of explanation, used specific nomenclature to provide a thorough understanding of the invention. However, it will be apparent to one skilled in the art that specific details are not required in order to practice the invention. Thus, the foregoing descriptions of specific aspects of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A surgical tool for a surgical robotic system, the surgical tool comprising:
a surgical tool grasper having a jaw operable to perform a surgical procedure;
a handle coupled to the surgical tool grasper and having a lever operable to actuate the jaw; and
an actuation combiner mechanism comprising a rotatable member coupled to the lever by a first input link coupled to the rotatable member at a first pivot point, a motor by a second input link coupled to the rotatable member at a second pivot point, and a movable yoke by an output link to combine an actuation force output of the lever with an actuation force output of the motor to control the operation of the jaw using the yoke or the lever.

2. The surgical tool of claim 1 wherein the rotatable member comprises a combiner wheel that rotates about a center pivot point and couples the first input link from the lever and the second input link from the motor to the output link that controls the operation of the jaw or the lever.

3. The surgical tool of claim 2 wherein the first pivot point is a first radial distance from the center pivot point and the second pivot point is a second radial distance from the center pivot point.

4. The surgical tool of claim 3 wherein a ratio of the first radial distance and the second radial distance are configured to be modified to change a ratio of the first radial distance to the second radial distance and modify the combined actuation force output.

5. The surgical tool of claim 3 wherein the combiner wheel comprises a radially oriented slot and the first pivot point or the second pivot point is defined by a pin operable to slide within the radially oriented slot to modify a distance of the first pivot point or the second pivot point to the center pivot point.

6. The surgical tool of claim 1 wherein the motor further comprises a sensor for determining a position of the jaw during an operation.

7. The surgical tool of claim 6 wherein the sensor is an encoder that detects a position of the motor to indirectly determine the position of the jaw during operation.

8. The surgical tool of claim 1 wherein the motor further comprises an actuator operable to output a micro modulation frequency to the output link of the actuation combiner mechanism.

9. The surgical tool of claim 1 further comprising a haptic feedback mechanism that provides a haptic output to a user corresponding to the operation of the jaw or the lever.

10. A motorized surgical tool for a surgical robotic system, the surgical tool comprising:
a surgical tool grasper having a jaw operable to perform a surgical procedure;
a handle coupled to the surgical tool grasper and having a lever operable to actuate the jaw; and
an actuation combiner mechanism comprising a combiner wheel, a lever input link coupled to the combiner wheel at a first pivot point and coupled to the lever, a motor input link coupled to the combiner wheel at a second pivot point and coupled to a motor, and an output link coupled to a yoke that causes the jaw to open or close.

11. The motorized surgical tool of claim 10 wherein a movement of the lever to a closed position produces an actuation force output of the lever in a first direction that causes the yoke to move the jaw to a closed position.

12. The motorized surgical tool of claim 11 wherein a movement of the lever to an open position produces an actuation force output of the lever in a second direction that causes the yoke to move the jaw to an open position.

13. The motorized surgical tool of claim 12 wherein the actuation combiner mechanism combines the actuation force output of the lever in the first direction or the second direction with an actuation force output of the motor to move the jaw.

14. The motorized surgical tool of claim 13 wherein the combined actuation force output of the lever and the motor is operable to be modified by modifying a ratio of a first radial distance of the first pivot point to a center of the combiner wheel and a second radial distance of the second pivot point to the center of the combiner wheel.

15. The motorized surgical tool of claim 14 wherein the combiner wheel comprises a radially oriented slot, and a pin defining the first pivot point is adjustable within the slot to modify the first radial distance.

16. The motorized surgical tool of claim 15 wherein the radially oriented slot is curved.

17. The motorized surgical tool of claim 13 wherein the combiner wheel comprises an elongated shape.

18. The motorized surgical tool of claim 10 wherein the motor further comprises an encoder that detects a position of the motor to indirectly determine the position of the jaw during operation.

19. The motorized surgical tool of claim 10 wherein the motor further comprises an actuator operable to output a micro modulation frequency to the output link.

20. The motorized surgical tool of claim 10 further comprising a haptic feedback mechanism that provides a haptic output to a user corresponding to the operation of the jaw.

* * * * *